(12) United States Patent
Schweder et al.

(10) Patent No.: US 9,453,010 B2
(45) Date of Patent: Sep. 27, 2016

(54) MARKER DYES FOR UV AND SHORT WAVE EXCITATION WITH HIGH STOKES SHIFT BASED ON BENZOXAZOLES

(71) Applicant: Dyomics GmbH, Jena (DE)

(72) Inventors: Bernd G. Schweder, Jena (DE); Matthias S. Wenzel, Jena (DE); Wilhelm G. Frank, Jena (DE); Frank G. Lehmann, Jena (DE); Peter T. Czerney, Weimar (DE)

(73) Assignee: DYOMICS GMBH, Jena (DE)

( * ) Notice: Subject to any disclaimer, the term of this patent is extended or adjusted under 35 U.S.C. 154(b) by 0 days.

(21) Appl. No.: 14/579,169

(22) Filed: Dec. 22, 2014

(65) Prior Publication Data
US 2015/0175591 A1  Jun. 25, 2015

(30) Foreign Application Priority Data

Dec. 23, 2013  (DE) .................. 10 2013 114 848

(51) Int. Cl.
| | |
|---|---|
| *C07D 413/04* | (2006.01) |
| *C07D 413/14* | (2006.01) |
| *C09B 62/00* | (2006.01) |
| *C07D 413/06* | (2006.01) |
| *G01N 33/58* | (2006.01) |

(52) U.S. Cl.
CPC ........... *C07D 413/14* (2013.01); *C07D 413/04* (2013.01); *C07D 413/06* (2013.01); *C09B 62/00* (2013.01); *G01N 33/582* (2013.01)

(58) Field of Classification Search
CPC .................................................. C07D 413/04
USPC ...................................................... 546/271.7
See application file for complete search history.

(56) References Cited

U.S. PATENT DOCUMENTS

| | | |
|---|---|---|
| 8,158,801 B2 | 4/2012 | Buller et al. |
| 8,178,360 B2 | 5/2012 | Barnes et al. |
| 8,415,477 B2 | 4/2013 | Buller et al. |
| 8,822,695 B2 | 9/2014 | Buller et al. |
| 2003/0165942 A1 | 9/2003 | Czerney et al. |
| 2007/0077549 A1 | 4/2007 | Buller et al. |
| 2010/0009353 A1 | 1/2010 | Barnes et al. |
| 2012/0004397 A1 | 1/2012 | Buller et al. |
| 2013/0273569 A1 | 10/2013 | Buller et al. |
| 2015/0050685 A1 | 2/2015 | Buller et al. |

FOREIGN PATENT DOCUMENTS

| | | |
|---|---|---|
| EP | 1318177 B1 | 6/2003 |
| EP | 1535969 B1 | 6/2005 |
| WO | 2007038659 A1 | 4/2007 |
| WO | 2007135368 A1 | 11/2007 |

OTHER PUBLICATIONS

Brinkley M. : "A Brief Survey of Methods for Preparing Protein Conjugates with Dyes, Haptens, and Cross-Linking Reagents", Bioconjugate Chem. 3 (1992), pp. 2-12.
Waggoner A. : "Covalent Labeling of Proteins and Nucleic Acids with Fluorophores", Meth. Enzymol., 246 (1995), pp. 362-373.
Poppe, E.-J.: "Sensibilisierungsfarbstoffe mit sauren N-Substituenten", Z. wiss. Photographie, 63 (1969), pp. 149-158.
Panchuk-Voloshina N. et al.: "Alexa Dyes, a Series of New Fluorescent Dyes that Yield Exceptionally Bright, Photostable Conjugates", J. Histochem. Cytochem., 47 (1999), pp. 1179-1188.
Imasaka, T. et al.: "Diode lasers in analytical chemistry", Talanta, 48 (1999), pp. 305-320.
Lee L. G. et al.: "Near-IR Dyes in Three-Color Volumetric Capillary Cytometry: Cell Analysis With 633- and 785 nm-Laser Excitation", Cytometry, 21 (1995), pp. 120-128.
Kubin, R.F. et al.: "Anionic and Zwitterionic Photophysical Effects in some Pyridinium Oxazole Laser Dyes", Laser Chemistry 1990, 10(4), pp. 247-258.
Fletcher et al.: "Fluorescence and lasing characteristics of some long-lived flashlamp-pumpable, oxazole dyes", Optics Communications, North-Holland Publishing Co. Amsterdam, NL, Br. 48, Nr. 5, Jan. 1, 1984, pp. 352-356.

*Primary Examiner* — Patricia L Morris
(74) *Attorney, Agent, or Firm* — Abel Law Group, LLP

(57) ABSTRACT

The invention concerns compounds based on benzoxazoles wherein selected substituents are each a reactive group A bound via a linker L and adapted to covalently bond a compound of the invention to a to-be-marked molecule K, wherein A is an amine, hydroxy or phosphoramidite function, a carboxylic acid, an alkyl or active ester derived therefrom; a carboxylic acid hydrazide; or a carboxylic acid amide where
K is a covalently bound component selected from the group haptenes, proteins (antibodies), low molecular weight drug compounds, peptides, nucleotides, nucleosides, DNA oligomers, polymers, and t is from 1 to 10, and
L is a linker selected from a group featuring —$(CH_2)_s$—, —$[(CH_2)_m$—$O]_p$—$(CH_2)_m$—, —$NR10$-$(CH_2)_s$—, —$O$—$(CH_2)_s$—, —$S$—$(CH_2)_s$—, —$NR10$-$C(O)$—$(CH_2)_s$—, —$NR10$-$C(O)$—$O$—$(CH_2)_s$—, —$NR10$-$C(O)$—$NR11$-$(CH_2)_s$— or —$SO_2$—$NR10$-$(CH_2)_s$—, wherein R10 and R11 are each independently hydrogen, alkyl and alkoxyalkyl (—$[(CH_2)_m$—$O]_p$—$CH_3$), ω-sulfoalkyl (—$(CH_2)_r$—$SO_3$), m represents the numbers of 2-5, p, r and s each independently represent the number of 1-10.

13 Claims, 7 Drawing Sheets

MARKER DYES FOR UV AND SHORT WAVE EXCITATION WITH HIGH STOKES SHIFT BASED ON BENZOXAZOLES

CROSS-REFERENCE TO RELATED APPLICATIONS

The present application claims priority under 35 U.S.C. §119 of German Patent Application No. 102013114848.4, filed Dec. 23, 2013, the entire disclosure of which is expressly incorporated by reference herein.

BACKGROUND OF THE INVENTION

1. Field of the Invention

The present invention relates to benzoxazole-based marker dyes for UV and short wave excitation having a large Stokes shift.

2. Discussion of Background Information

Fluorescence-based markers have been used for decades in biological, biotechnological and medical research and also in medical diagnostics [Brinkley M., A Brief Survey of Methods for Preparing Protein Conjugates with Dyes, Haptens and Cross-Linking Reagents, Bioconjugate Chem, 3 (1992) 2-12; Waggoner A., Covalent Labeling of Proteins and Nucleic Acids with Fluorophores, Meth. Enzymol., 246 (1995) 362-373]. Originally, chromophores known from the field of textile and sensitizer dyes were derivatized to optimize them for applications in the aqueous physiological milieu. Developments here were focused in particular on solubility in water and also a high quantum yield in aqueous solution, the starting point for such development work usually being a film dye [Poppe E.-J., Sensibilisierungsfarbstoffe mit sauren N-Substituenten, Z. wiss. Photographie, 63 (1969) 149-158 and references cited therein].

Classes of dyes frequently used here are the xanthylium (fluorescein, rhodoles, rhodamines), cyanine (carbo, di-carbo and tri-carbo), dipyrrhomethene (BoDiPy) and coumarin chromophores, although the diversity of dyes is not restricted to the types referred to [Panchuk-Voloshina N. et al., Alexa Dyes, a Series of New Fluorescent Dyes that Yield Exceptionally Bright, Photostable Conjugates, J. Histochem. Cytochem., 47 (1999) 1179-1188].

Proceeding from commercially available light sources such as mercury and xenon burners and also tungsten lamps and constrained by the spectral limitation to the light which is visible to the human eye, fluorescent markers were first developed for chromophores emitting between 400 nm and about 650 nm.

The advent of lasers as excitation light sources opened up completely new possibilities of spectral combination far beyond the visible region on the dye side as well as for the optical detection to be realized on the equipment side, owing to the high intensity of lasers leading to a significantly enhanced sensitivity on the part of the measuring instruments. In addition to conventional lasers, the virtually monochromatic light-emitting diodes (LEDs) and solid-state laser diodes [Imasaka T., Diode lasers in analytical chemistry, Talanta, 48 (1999) 305-320] are still becoming more and more important in the fluorescence-based detection for bioanalytical applications.

The motivation to glean more and more information from bioanalytical procedures finds expression in multicolor analyses that have become part of routine laboratory practice, for example in flow cytometry [Lee L. G., NEAR-IR Dyes in Three Color Volumetric Capillary Cytometry: Cell Analysis With 633- and 785-nm Laser Excitation, Cytometry, 21 (1995) 120-128], DNA sequencing and various PCR methods (Roche's LightCycler). Dye combinations were initially used here to deliver spectrally distinguishable signals on excitation by one and the same (monochromatic) light source via energy transfer from a donor to various acceptors. Examples thereof are the DNA sequencers from Amersham (now GE Healthcare) and ABI (now Life Technologies), which came on the market at the end of the 1990s.

DNA and RNA in the present description refer to deoxyribonucleic acid and ribonucleic acid respectively.

An alternative approach to multiplex applications is to use dyes that permit spectral differentiation without energy transfer between donor and acceptor. Examples thereof are found in the MegaStokes dyes known since about 2002 (EP 1 318 177 B1, EP 1 535 969 B1). These are preferentially tailored to an excitation wavelength between 470 nm (cyan LEDs) and 500 nm (488 nm Ar-ion lasers) to best meet the then state of the art in excitation light sources.

Similarly the combination of two or more excitation light sources with more than one chromphore per light source is now established prior art (Solexa, WO2007/135,368A2). A typical application here is Next Generation Sequencing (NGS).

The availability of light-intensive, short-wave excitation sources such as UV-LEDs or violet laser diodes also widened the base of suitable fluorophores for bioanalytical applications. One example thereof is Pacific Orange from Molecular Probes (U.S. Pat. No. 8,158,801), which similarly to the MegaStokes™ dyes permitted multicolor analyses in combination with coumarin-based chromophores, albeit on excitation at around 400 nm.

The invention has as its object the provision of benzoxazole-based fluorescent markers having a large Stokes shift, a high photo and storage stability and also a high fluorescence quantum yield.

SUMMARY OF THE INVENTION

The present invention describes marker dyes based on benzoxazoles of the general structure

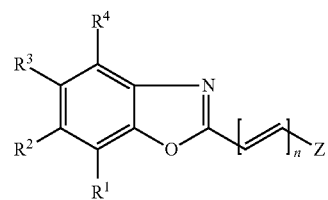

and their salts, wherein Z is either

Z=4-pyridyl

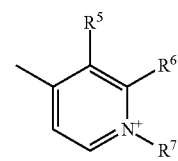

to form structure I, or

Z=3-pyridyl

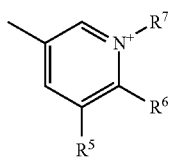

to form structure II, or
Z=2-pyridyl

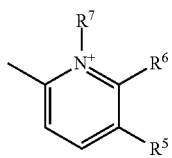

to form structure III,
and R2 and/or R7 are each a reactive group A bound via a linker L and adapted to covalently bind a compound of structure I, II or III to a to-be-marked molecule K, wherein A is an amine (—$NH_2$), hydroxyl (—OH) or phosphoramidite function (—O—P—[O—$CH_2$—$CH_2$—CN]—N[(CH($CH_3$)$_2$)$_2$]), a carboxylic acid (—COOH), an alkyl or active ester derived therefrom (NHS ester, sulfo-NHS ester, tetrafluorophenyl ester, p-sulfotetrafluorophenyl ester); a carboxylic hydrazide (—$CONHNH_2$); or a carboxylic amide (—CONHR12)
where R12 is —$(CH_2)_r$—Y, wherein
Y is —OH, —$NH_2$, —$NH_3^+$, maleimide (—N[CO—$CH_2$]$_2$), —NCS, —NCO, —NH—CO—$CH_2$—I, —NH—CO—$CH_2$—Br, azide (—N3), alkyne (—CCH) or phosphoramidite (—O—P—[O—$CH_2$—$CH_2$—CN]—N—[CH—($CH_3$)$_2$]$_2$), and
K is a covalently bound component selected from the group haptens (molecules which represent an incomplete antigen and only display the action of an antigen on binding to proteins or cell structures), proteins, antibodies (proteins formed in response to antigens), low molecular weight drug compounds (active pharmaceutical ingredients which by virtue of their relatively low molar mass of up to about 800 g/mol are capable, unlike for example proteins as very large molecules, of penetrating into cells), peptides (small or short-chain proteins of up to about 100 linked amino acids), nucleotides (basic building blocks of nucleic acids such as DNA or RNA, which consist of a phosphate part, a monosaccharide part and a nucleobase part such as adenine, guanine, cytosine, thymine or uracil), nucleosides (basic building blocks of nucleic acids such as DNA or RNA which do not have a phosphate part but only consist of a monosaccharide part and a nucleobase part), DNA oligomers (unlike the DNA macromolecule, molecules of deoxyribonucleic acid with a relatively low, unspecified number of nucleotides), polymers (synthetic or natural chain-shaped or branched chemical compounds of repeating units, the monomers. Polymers may in the form of copolymers also consist of two or more different monomers in different quantitative ratios and arrangements) and
L is a linker selected from a group featuring —$(CH_2)_s$—, —$[(CH_2)_m$—O$]_p$—$(CH_2)_m$—, NR10-$(CH_2)_s$—, —O—$(CH_2)_s$—, —S—$(CH_2)_s$—, —NR10-C(O)—$(CH_2)_s$—, —NR10-C(O)—O—$(CH_2)_s$—, —NR10-C(O)—NR11-$(CH_2)_s$— or —$SO_2$—NR10-$(CH_2)_s$—, wherein R10 and R11 are each independently hydrogen, alkyl and alkoxyalkyl (—$[(CH_2)_m$—O$]_p$—$CH_3$), ω-sulfoalkyl (—$(CH_2)_r$—$SO_3$), m represents the numbers 2-5, p, r and s each independently represent the numbers from 1-10.

Disclosed are compounds of structure I and their salts with n=0 or 1, wherein
R1 and R3-R6 are each independently hydrogen, halogen or a sulfonic acid moiety,
R2 is ω-sulfoalkoxy (—O—$(CH_2)_r$—$SO_3$), alkoxy, polyalkoxy (—O—$[(CH_2)_m$—O$]_p$—$CH_3$), an amine function (—NR8R9), wherein R8 and R9 are each independently hydrogen, alkyl, ω-sulfoalkyl (—$(CH_2)_r$—$SO_3$), —CO-alkyl, —CO—NR10-alkyl or –CO—O-alkyl or equal to -LA where L is —NR10-C(O)—$(CH_2)_s$—, —NR10-C(O)—NR11-$(CH_2)_s$—,
R10 and R11 are each independently hydrogen, alkyl, alkoxy, polyalkoxy (—O—$[(CH_2$—O$)_m]_p$—$CH_3$) or ω-sulfoalkyl (—$(CH_2)_r$—$SO_3$),
R7 is -LA where L is —$(CH_2)_s$— or —$[(CH_2)_m$—O$]_p$—$(CH_2)_m$— or equal to ω-sulfoalkyl (—$(CH_2)_r$—$SO_3$),
A is an amine (—$NH_2$), hydroxy (—OH) or phosphoramidite function (—O—P—[O—$CH_2$—$CH_2$—CN]—N[(CH($CH_3$)$_2$)$_2$]), a carboxylic acid (—COOH) or derivatives derived therefrom as under claim 1
m is 2-5, and
p, r and s are each independently 1-10.

Further disclosed are compounds of structure I and their salts with
n=0 or 1, wherein
R1, R2, R5 and R6 are each hydrogen or a sulfonic acid moiety, and
R3-R4 are bridged —(CR13=CR14)$_2$-, wherein R13 and R14 are each independently hydrogen and/or a sulfonic acid moiety,
R7 is -LA where L is —$(CH_2)_s$— or —$[(CH_2)_m$—O$]_p$—$(CH_2)_m$—,
A is an amine (—$NH_2$), hydroxy (—OH) or phosphoramidite function (—O—P—[O—$CH_2$—$CH_2$—CN]—N[(CH($CH_3$)$_2$)$_2$]), a carboxylic acid (—COOH) or derivatives derived therefrom as under claim 1
m is 2-5, and
p and s are each independently 1-10.

Also disclosed are compounds of structure I and their salts with
n=0 or 1, wherein
R1, R3 and R4 are each hydrogen, halogen or a sulfonic acid moiety, and
R5-R6 are bridged —(CR13=CR14)$_2$-, wherein R13 and R14 are each independently hydrogen and/or a sulfonic acid moiety,
R2 is sulfoalkoxy (—O—$(CH_2)_r$—$SO_3$), alkoxy or polyalkoxy (—O—$[(CH_2)_m$—O$]_p$—$CH_3$),
R7 is -LA where L is —$(CH_2)_s$— or —$[(CH_2)_m$—O$]_p$—$(CH_2)_m$—,
A is an amine (—$NH_2$), hydroxy (—OH) or phosphoramidite function (—O—P—[O—$CH_2$—$CH_2$—CN]—N[(CH($CH_3$)$_2$)$_2$]), a carboxylic acid (—COOH) or derivatives derived therefrom as under claim 1
m is 2-5, and
p, r and s are each independently 1-10,
and also compounds of structure I and their salts with
n=0 or 1, wherein
R1 and R2 are each hydrogen or a sulfonic acid moiety, and
R3-R4 and R5-R6 are each bridged —(CR13=CR14)$_2$-, wherein R13 and R14 are each independently hydrogen and/or a sulfonic acid moiety, R7 is -LA where L is —(CH$_2$)$_s$— or —[(CH$_2$)$_m$—O]$_p$—(CH$_2$)$_m$—,
A is an amine (—NH$_2$), hydroxy (—OH) or phosphoramidite function (—O—P—[O—CH$_2$—CH$_2$—CN]—N[CH(CH$_3$)$_2$]$_2$), a carboxylic acid (—COOH) or a derivative derived therefrom as under claim 1
m is 2-5, and
p and s are each independently 1-10.

And also compounds of structure II and their salts with n=0 or 1, wherein
R1 and R3-R6 are each independently hydrogen, halogen or a sulfonic acid moiety,
R2 is ω-sulfoalkoxy (—O—(CH$_2$)$_r$— SO$_3$), alkoxy, polyalkoxy (—O—[(CH$_2$)—O)$_m$]$_p$—CH$_3$), an amine function (—NR8R9), wherein R8 and R9 are each independently hydrogen, alkyl, ω-sulfoalkyl (—(CH$_2$)$_r$—SO$_3$), —CO-alkyl, —CO—NR10-alkyl or –CO—O-alkyl or equal to -LA where L is —NR10-C(O)—(CH$_2$)$_s$—, —NR10-C(O)—NR11-(CH$_2$)$_s$—,
R10 and R11 are each independently hydrogen, alkyl, alkoxy, polyalkoxy (—O—[(CH$_2$—O)$_m$]$_p$—CH$_3$) or ω-sulfoalkyl (—(CH$_2$)$_r$—SO$_3$),
R7 is -LA where L is —(CH$_2$)$_s$— or —[(CH$_2$)$_m$—O]$_p$—(CH$_2$)$_m$— or equal to ω-sulfoalkyl (—(CH$_2$)$_r$—SO$_3$),
A is an amine (—NH$_2$), hydroxy (—OH) or phosphoramidite function (—O—P—[O—CH$_2$—CH$_2$—CN]—N[CH(CH$_3$)$_2$]$_2$), a carboxylic acid (—COOH) or derivatives derived therefrom
m is 2-5, and
p, r and s are each independently 1-10.

And also the compound of structure III and its salts with n=0 or 1, wherein
R1 and R3-R6 are each independently hydrogen, halogen or a sulfonic acid moiety,
R2 is ω-sulfoalkoxy (—O—(CH$_2$)$_r$— SO$_3$), alkoxy, polyalkoxy (—O—[(CH$_2$)$_m$—O]$_p$—CH$_3$), an amine function (—NR8R9), wherein R8 and R9 are each independently hydrogen, alkyl, ω-sulfoalkyl (—(CH$_2$)$_r$—SO$_3$), —CO-alkyl, or –O—CO-alkyl
or equal to -LA where L is —NR10-C(O)—(CH$_2$), —, —NR10-C(O)—NR11-(CH$_2$)$_s$—,
R10 and R11 are each independently hydrogen, alkyl, alkoxy, polyalkoxy (—O—[(CH$_2$—O)$_m$]$_p$—CH$_3$) or ω-sulfoalkyl (—(CH$_2$)$_r$—SO$_3$),
R7 is -LA where L is —(CH$_2$)$_s$— or —[(CH$_2$)$_m$—O]$_p$—(CH$_2$)$_m$— or equal to ω-sulfoalkyl (—(CH$_2$)$_r$—SO$_3$),
A is an amine (—NH$_2$), hydroxy (—OH) or phosphoramidite function (—O—P—[O—CH$_2$—CH$_2$—CN]—N[CH(CH$_3$)$_2$]$_2$), a carboxylic acid (—COOH) or derivatives derived therefrom as under claim 1
m is 2-5, and
p, r and s are each independently 1-10.

And also compounds of structure III and their salts with n=0 or 1, wherein
R1, R2, R5, R6 are each hydrogen or a sulfonic acid moiety, and
R3-R4 are bridged —(CR13=CR14)$_2$-, wherein R13 and R14 are each independently hydrogen and/or a sulfonic acid moiety,
R7 is -LA where L is —(CH$_2$)$_s$— or —[(CH$_2$)$_m$—O]$_p$—(CH$_2$)$_m$—,
A is an amine (—NH$_2$), hydroxy (—OH) or phosphoramidite function (—O—P—[O—CH$_2$—CH$_2$—CN]—N[CH(CH$_3$)$_2$]$_2$), a carboxylic acid (—COOH) or derivatives derived therefrom as under claim 1
m is 2-5, and
p and s are each independently 1-10.

And also compounds of structure III and their salts with n=0 or 1, wherein
R1, R3, R4 are each hydrogen, halogen or a sulfonic acid moiety, and
R5-R6 are bridged —(CR13=CR14)$_2$-, wherein R13 and R14 are each independently hydrogen and/or a sulfonic acid moiety,
R2 is ω-sulfoalkoxy (—O—(CH$_2$)$_r$— SO$_3$), alkoxy or polyalkoxy (—O—[(CH$_2$)$_m$—O]$_p$—CH$_3$),
R7 is -LA where L is —(CH$_2$)$_s$— or —[(CH$_2$)$_m$—O]$_p$—(CH$_2$)$_m$—,
A is an amine (—NH$_2$), hydroxy (—OH) or phosphoramidite function (—O—P—[O—CH$_2$—CH$_2$—CN]—N[CH(CH$_3$)$_2$]$_2$), a carboxylic acid (—COOH) or derivatives derived therefrom as under claim 1
m is 2-5, and
p, r and s are each independently 1-10.

And also compounds of structure III and their salts with n=0 or 1, wherein
R1, R2 are each hydrogen or a sulfonic acid moiety, and
R3-R4 and R5-R6 are bridged —(CR13=CR14)$_2$-, wherein R13 and R14 are each independently hydrogen and/or a sulfonic acid moiety,
R7 is -LA where L is —(CH$_2$)$_s$— or —[CH$_2$)$_m$—O]$_p$—(CH$_2$)$_m$—,
A is an amine (—NH$_2$), hydroxy (—OH) or phosphoramidite function (—O—P—[O—CH$_2$—CH$_2$—CN]—N[CH(CH$_3$)$_2$]$_2$), a carboxylic acid (—COOH) or derivatives derived therefrom as under claim 1
m is 2-5, and
p and s are each independently 1-10.

Compounds of structures I to III with A in the form of an active ester are described, wherein the active ester is an NHS ester (N-hydroxysuccinimidyl ester), a sulfo-NHS ester (sulfo-hydroxysuccinimidyl ester), a TFP ester (tetrafluorophenyl ester) or an STP ester (p-sulfotetrafluorophenyl ester).

Also described are compounds of structures I to III wherein A is in the form of a carboxylic acid derivative, and/or compounds of structures I to III wherein A is in the form of a phosphoramidite wherein A is a group of the formula

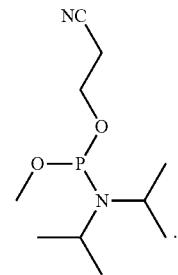

The disclosed compounds of structures I to III are useful as marker dyes based on benzoxazoles the to-be-marked molecules K being bonded to a compound of structure I, II or III via the linker L and the reactive group A.

Compounds of structures I to III are further described, characterized in that R1 and R2 and/or R2 and R3 and/or R3 and R4 and/or R5 and R6 are each independently bonded together to form fused aromatic rings substituted with hydrogen and/or sulfo radical.

Corresponding core structures, which are usually soluble in organic solvents only and are devoid of any functionality making the covalent attachment of, for example, biomolecules (chemical compounds that occur in living matter and are essential inter alia for the metabolism and regulatory mechanisms) have been described in the literature (e.g., R. F. Kubin et al. 1990, Laser Chemistry 10 (4): 247-58). The fluorophores have to have a fluorescence that is independent of the pH and other environmental influences (solvent polarity, for example), be soluble in protic solvents and also be able to form a covalent bond with a suitable biomolecule under physiological conditions.

The prerequisite for employment as a fluorescent marker is the formation of a covalent bond with a suitable biomolecule via the presence of an activated carboxylic acid, of an activated hydroxy group and/or of a primary amino function. Good solubility in water requires the presence of polar substituents, in particular sulfonic acid substituents, in the molecule. The sulfonic acid substituents also influence the aggregation characteristics (noncovalent dimerization and also noncovalent attachment to biomolecules and surfaces). Sulfonic acid substituents bonded directly to a dye's core structure also influence the physical-chemical properties of the dyes by shifting the absorption and emission wavelengths hypsochromically and generally causing a significant increase in quantum yield.

The benzoxazoles of structures I-III are useful as dyes for optical marking of organic or inorganic recognition units, for example of amino acids, peptides, proteins, antigens, haptens, enzyme substrates, enzyme cofactors, biotin, carotenoids, hormones, neurohormones, neurotransmitters, growth factors, lectins, toxins, carbohydrates, oligosaccharides, polysaccharides, dextrans, nucleic acids, oligonucleotides, DNA, RNA, biological cells, lipids, receptor-binding drugs or organic and/or inorganic polymeric carrier materials.

Marking the recognition units may be effected by the formation of ionic or van der Waals interactions between the markers of structures I-III and the materials to be marked.

The recognition unit or the carrier material may further also be bonded covalently to the fluorophore. This coupling reaction may be carried out in aqueous or predominantly aqueous solution and preferably at room temperature. The product formed is a fluorescent probe (conjugate) for qualitative or quantitative determination of different biomaterials and/or other organic and inorganic materials.

Both the compounds of structures I-III and the systems derived therefrom are useful in optical, particularly fluorescence-optical, qualitative and quantitative assays to diagnose cell properties, in biosensors (point-of-care measurements), to explore the genome (DNA sequencing) and in miniaturization technologies. Typical applications are in cytometry and cell sorting, fluorescence correlation spectroscopy (FCS), in ultra-high throughput screening (UHTS), in multicolor fluorescence-in-situ hybridization (FISH) and in microarrays (DNA and protein chips).

A microarray in this context is a grid-shaped arrangement of molecules immobilized on at least one surface which are useful for studying receptor-ligand interactions. A grid-shaped arrangement is to be understood as meaning more than two mutually different molecules present within an area and immobilized therein in different, previously defined regions of known position.

A receptor is a molecule with an affinity for a given ligand. Receptors may be naturally occurring or artificially produced molecules. Receptors may be used in pure form or attached to other species. Receptors may be linked to some entity covalently or noncolvalently either directly or through certain promoters of coupling.

Examples of receptors detectable by this invention include agonists and antagonists for cell membrane receptors, toxins and other poisonous materials, viral epitopes, hormones such as opiates and steroids, hormone receptors, peptides, enzymes, enzyme substrates, cofactors in the form of actives, lectins, sugars, oligonucleotides, nucleic acids, oligosaccharides, cells, cell fragments, tissue fragments, proteins and antibodies, but are not restricted to the recited entities.

A ligand is a molecule which is recognized by a certain receptor. Examples of ligands detectable by this invention include agonists and antagonists for cell membrane receptors, toxins and other poisonous materials, viral epitopes, hormones such as opiates and steroids, hormone receptors, peptides, enzymes, enzyme substrates, cofactors in the form of actives, lectins, sugars, oligonucleotides, nucleic acids, oligosaccharides, proteins and antibodies, but are not restricted to the recited entities.

The preparation of benzoxazoles provides the following advantages in particular:

Given suitable substitution, the absorption maxima reside in the emission range of the laser wavelength of UV lasers (<400 nm) and the emission maxima are observed in the range between 450 and 660 nm. FIG. 1 demonstrates the different emission bands of selected dyes in accordance with the present invention, wherein the extinction at an excitation wavelength of 370 nm is not less than 75% of the maximum excitation efficiency.

A further advantage is that the hydrophilic character of the differently emitting fluorophores can be varied to an almost infinite extent.

Compounds of the present invention may have at least one reactive group A in the form of an active ester, wherein the active ester is an NHS ester (N-hydroxysuccinimidyl ester), a sulfo-NHS ester (sulfo-hydroxysuccinimidyl ester), a TFP ester (tetrafluorophenyl ester) or an STP ester (p-sulfotetrafluorophenyl ester), as indicated in the following table:

| A | Active ester |
|---|---|
| (structure) | NHS |
| (structure) | Sulfo-NHS |
| (structure) | TFP |

-continued

| A | Active ester |
|---|---|
| 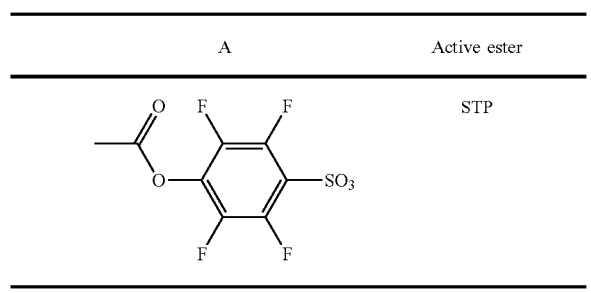 | STP |

The compounds of the present invention in other embodiments may have A in the form of a carboxylic acid derivative, in which case the carboxylic acid derivative is a hydrazide, an amine, an iodoacetamide, a maleimide, an alkyne or an azide, as indicated in the following table:

| A | Carboxamide derivatives |
|---|---|
| 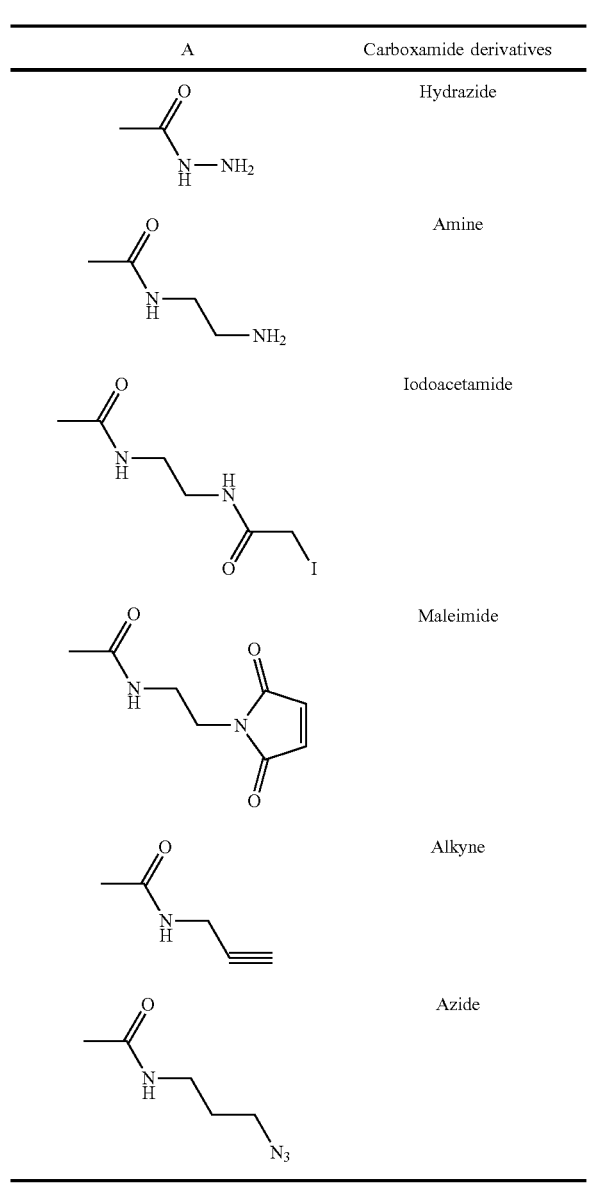 | Hydrazide |
| | Amine |
| | Iodoacetamide |
| | Maleimide |
| | Alkyne |
| | Azide |

The invention will now be more particularly described by means of working examples and drawings. Shown are:

Figure 1A:
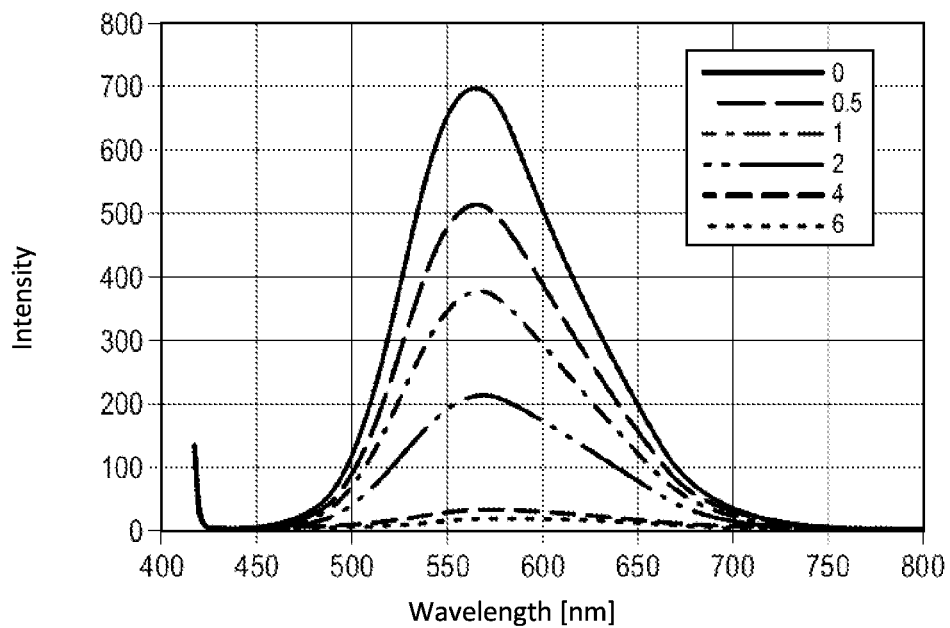
FIG. 1A fluorescence quenching by energy transfer for compound 19/DYQ-1
A) Binding pair of streptavidin/biotin,
FIG. 1B fluorescence quenching by energy transfer for compound 19/DYQ-1
B) blank sample (streptavidin/free acid),
FIG. 2 absorption and emission spectra of compound 22,
FIG. 3 absorption and emission spectra of compound 1,
FIG. 4 absorption and emission spectra of compound 17,
FIG. 5 absorption and emission spectra of compound 19,
FIG. 6 absorption and emission spectra of compound 21, and
FIG. 7 emission spectra of selected dyes of the present invention.

The curve trajectories in FIGS. 1A to 7 represent the closest possible fit to the actual measurements.

DETAILED DESCRIPTION OF THE INVENTION

Working Example 1

1-(5-Carboxypentyl)-4-[6-(3-sulfonatopropoxy)benzooxazol-2-yl]pyridinium betaine Precursor 1: 2-Pyridin-4-yl-benzooxazol-6-ol

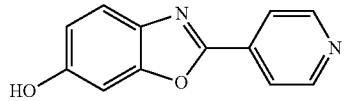 [SMILES: Oc1ccc2nc(-c3ccncc3)oc2c1]

2.0 g of 4-aminoresorcinol hydrochloride, 1.52 g of isonicotinic acid and 5 g of trimethylsilyl polyphosphate are heated in 20 ml of 1,2-dichlorobenzene and 2.11 ml of ethyldiisopropylamine to 180° C. for 6 hours. Cooling is followed by suspending with 70 ml of dichloromethane and neutralizing by admixture of 50 ml of 1N NaOH solution. This is followed by treatment in an ultrasonication bath until there is a pale gray fine precipitate, which is filtered, washed with a little water and dried. Yield: 745 mg (28%) ($C_{12}H_8N_2O_2$, 212.21 g/mol)
MS ESI−(m/z): 211 (base, [M+H]−)

Precursor 2: 1-(5-Ethoxycarbonylpentyl)-4-(6-hydroxybenzooxazol-2-yl)pyridinium bromide

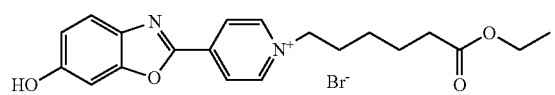 [SMILES: CCOC(=O)CCCCC[n+]1ccc(-c2nc3ccc(O)cc3o2)cc1 ; [Br-]]

445 mg of precursor 1 are stirred with 500 mg of ethyl 6-bromohexanoate in 8 ml of DMF at 150° C. for 24 hours. After cooling, 40 ml of diethyl ether is added to bring down an oil, which is discarded. The organic solvent is distilled off and the residue is purified by RP chromatography.
Yield: 605 mg (64%) ($C_{20}H_{23}N_2O_4{}^+Br^-$, 435.32 g/mol)
MS ESI+(m/z): 355 (base, [M]+)

Precursor 3: 1-(5-Carboxypentyl)-4-(6-hydroxybenzooxazol-2-yl)pyridinium bromide

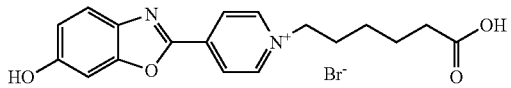 [SMILES: O=C(O)CCCCC[n+]1ccc(-c2nc3ccc(O)cc3o2)cc1 ; [Br-]]

600 mg of precursor 2 are refluxed in 3M HCl for 1 hour. After cooling, the solution is neutralized with sodium bicarbonate. Purification is by RP chromatography.

Yield: 480 mg (85%) ($C_{18}H_{19}N_2O_4^+Br^-$, 407.26 g/mol)
MS ESI+(m/z): 327 (base, $[M]^+$)
UV-Vis in PBS: $\lambda_{max}$: 385 nm, $\lambda_{em}$: 495 nm, c=19.400 l/mol*cm, QY: 0.02
Compound 1:

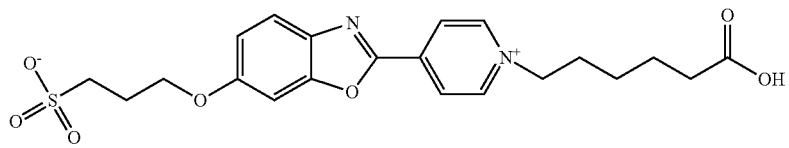 [SMILES: O=C(O)CCCCC[n+]1ccc(-c2nc3ccc(OCCCS(=O)(=O)[O-])cc3o2)cc1]

300 mg of precursor 3 are stirred in 3 ml of DMF together with 118 mg of propanesultone and 70 mg of potassium bicarbonate at 100° C. for 5 hours. To cleave the ester, the gellike mixture is admixed with 20 ml of 3M HCl and refluxed for 1 hour. Neutralization with sodium bicarbonate is followed by purification via RP chromatography.

Yield: 125 mg (42%) ($C_{21}H_{24}N_2O_7S$, 448.50 g/mol)
MS ESI-(m/z): 447 (base, $[M+H]^-$), 895 (30%, $[2M-H]^-$)
MS ESI+(m/z): 449 (base, $[M+H]^+$), 471 (15%, $[M+Na]^+$)
UV-Vis in PBS: $\lambda_{max}$: 383 nm, $\lambda_{em}$: 516 nm (cf. FIG. 3), c=22.000 l/mol*cm, QY: 0.70
$^1$H NMR 400 MHz (d6-DMSO) δ (ppm): 12.05 (S, 1H, COOH), 9.23 (D, 2H, pyridyl-H), 8.69 (D, 2H, pyridyl-H), 7.86 (D, 1H, benzoxazole-H), 7.51 (D, 1H, benzoxazole-H), 7.14 (D, 1H, benzoxazole-H), 4.66 (T, 2H, N—CH$_2$—), 4.23 (T, 2H, O—CH$_2$—), 2.59 (M, 2H, —CH$_2$—COOH), 2.24 (M, 2H, —CH$_2$—SO3$^-$), 2.06 (M, 2H, —CH$_2$—), 1.97 (M, 2H, —CH$_2$—), 1.56 (M, 2H, —CH$_2$—), 1.33 (M, 2H, —CH$_2$—)

Working Example 2

1-(5-Carboxypentyl)-4-[5-chloro-6-(3-sulfonatopropoxy)benzooxazol-2-yl]pyridinium betaine Precursor 1:
5-Chloro-2-pyridin-4-ylbenzooxazol-6-ol

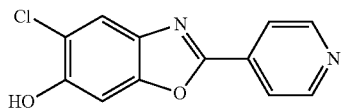

2.42 g of 4-amino-6-chloro-1,3-benzenediol hydrochloride, 1.52 g of isonicotinic acid and 5 g of trimethylsilyl polyphosphate are heated in 20 ml of 1,2-dichlorobenzene and 2.11 ml of ethyldiisopropylamine to 180° C. for 6 hours. Cooling is followed by suspending with 70 ml of dichloromethane and neutralizing by admixture of 50 ml of 1N NaOH solution. This is followed by treatment in an ultrasonication bath until there is a pale gray fine precipitate, which is filtered, washed with a little water and dried. Yield: 560 mg (18%) ($C_{12}H_7ClN_2O_2$, 246.65 g/mol)

MS ESI-(m/z): 245 (base, $[M-H]^-$)

Precursor 2: 4-(5-Chloro-6-hydroxybenzooxazol-2-yl)-1-(5-ethoxycarbonylpentyl)pyridinium bromide

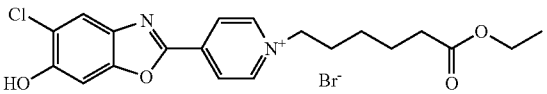

520 mg of precursor 1 are stirred with 500 mg of ethyl 6-bromohexanoate in 8 ml of DMF at 150° C. for 24 hours. After cooling, 40 ml of diethyl ether is added to bring down an oil, which is discarded. The organic solvent is distilled off and the residue is purified by RP chromatography.

Yield: 720 mg (72%) ($C_{20}H_{22}ClN_2O_4^+Br^-$, 469.76 g/mol)
MS ESI+(m/z): 389 (base, $[M]^+$)

Precursor 3: 1-(5-Carboxypentyl)-4-(5-chloro-6-hydroxybenzooxazol-2-yl)pyridinium bromide

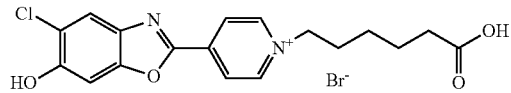 [SMILES: O=C(O)CCCCC[n+]1ccc(-c2nc3cc(Cl)c(O)cc3o2)cc1 ; [Br-]]

650 mg of precursor 2 are refluxed in 3M HCl for 1 hour. After cooling, the solution is neutralized with sodium bicarbonate. Purification is by RP chromatography.

Yield: 490 mg (80%) ($C_{18}H_{18}ClN_2O_4^+Br^-$, 441.71 g/mol)
MS ESI+(m/z): 361 (base, $[M]^+$)
UV-Vis in PBS: $\lambda_{max}$: 465 nm, $\lambda_{em}$: 655 nm, c=19.800 l/mol*cm, QY: 0.01

Compound 2:

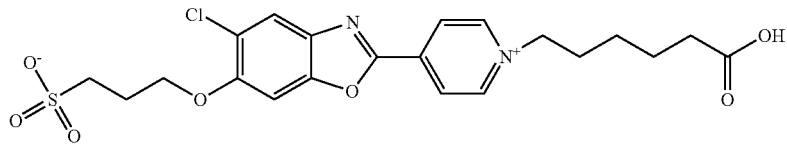 [SMILES: O=C(O)CCCCC[n+]1ccc(-c2nc3cc(Cl)c(OCCCS(=O)(=O)[O-])cc3o2)cc1]

325 mg of precursor 3 are stirred in 3 ml of DMF together with 118 mg of propanesultone and 70 mg of potassium bicarbonate at 100° C. for 5 hours. To cleave the ester, the gellike mixture is admixed with 20 ml of 3M HCl and refluxed for 1 hour. Neutralization with sodium bicarbonate is followed by purification via RP chromatography.

Yield: 135 mg (38%) ($C_{21}H_{23}ClN_2O_7S$, 482.94 g/mol)

MS ESI+(m/z): 483 (base, $[M+H]^+$), 485 (30%, $[M+H\,^{37}Cl]^+$)

UV-Vis in PBS: $\lambda_{max}$: 375 nm, $\lambda_{em}$: 505 nm, c=22.000 l/mol*cm; QY: 0.92

Working Example 3

1-(5-Carboxypentyl)-4-[5-chloro-6-(3-sulfonatopropoxy)benzooxazol-2-yl]pyridinium betaine Precursor 1: 5,7-Dichloro-2-(3-chloropyridin-4-yl)benzooxazol-6-ol

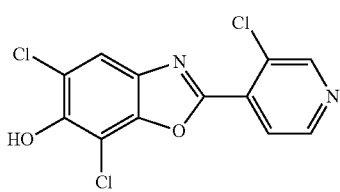 [SMILES: Oc1c(Cl)cc2nc(-c3ccncc3Cl)oc2c1Cl]

2.85 g of 4-amino-2,6-chlorobenzene-1,3-diol hydrochloride, 1.95 g of 3-chloropyridine-4-carboxylic acid and 5 g of trimethylsilyl polyphosphate are heated in 20 ml of 1,2-dichlorobenzene and 2.11 ml of ethyldiisopropylamine to 180° C. for 6 hours. Cooling is followed by suspending with 70 ml of dichloromethane and neutralizing by admixture of 50 ml of 1N NaOH solution. This is followed by treatment in an ultrasonication bath until there is a pale gray fine precipitate, which is filtered, washed with a little water and dried. Yield: 930 mg (23%)

($C_{12}H_5Cl_3N_2O_2$, 315.54 g/mol)

MS ESI-(m/z): 314 (base, $[M-H]^-$), 316 (90%, $[M-H]^-$), 318 (30%, $[M-H]^-$)

Precursor 2: 3-Chloro-4-(5,7-dichloro-6-hydroxy-benzooxazol-2-yl)-1-(5-ethoxycarbonylpentyl)-pyridinium bromide

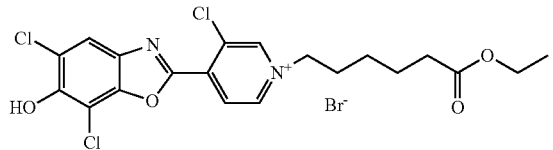 [SMILES: CCOC(=O)CCCCC[n+]1ccc(-c2nc3cc(Cl)c(O)c(Cl)c3o2)c(Cl)c1 ; [Br-]]

670 mg of precursor 1 are stirred with 500 mg of ethyl 6-bromohexanoate in 8 ml of DMF at 150° C. for 24 hours. After cooling, 40 ml of diethyl ether is added to bring down an oil, which is discarded. The organic solvent is distilled off and the residue is purified by RP chromatography.

Yield: 570 mg (50%) ($C_{20}H_{20}Cl_3N_2O_4^+Br^-$, 538.65 g/mol)

MS ESI-(m/z): 456 (base, $[M-H]^-$), 458 (95%, $[M-H]^-$), 460 (40%, $[M-H]^-$)

Precursor 3: 1-(5-Carboxypentyl)-3-chloro-4-(5,7-dichloro-6-hydroxybenzooxazol-2-yl)pyridinium bromide

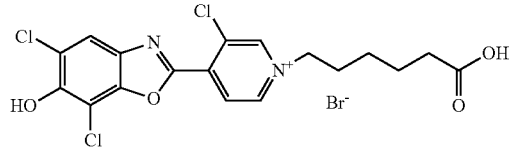 [SMILES: O=C(O)CCCCC[n+]1ccc(-c2nc3cc(Cl)c(O)c(Cl)c3o2)c(Cl)c1 ; [Br-]]

560 mg of precursor 2 are refluxed in 3M HCl for 1 hour. After cooling, the solution is neutralized with sodium bicarbonate. Purification is by RP chromatography.

Yield: 430 mg (82%) ($C_{18}H_{16}Cl_3N_2O_4^+Br^-$, 510.60 g/mol)

MS ESI-(m/z): 428 (base, $[M-H]^-$), 430 (95%, $[M-H]^-$), 432 (35%, $[M-H]^-$)

UV-Vis in PBS: $\lambda_{max}$: 462 nm, $\lambda_{em}$: 650 nm, c=19.200 l/mol*cm, QY: 0.04

Compound 3:

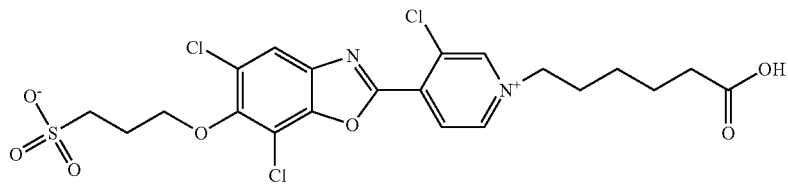 [SMILES: O=C(O)CCCCC[n+]1ccc(-c2nc3cc(Cl)c(OCCCS(=O)(=O)[O-])c(Cl)c3o2)c(Cl)c1]

380 mg of precursor 3 are stirred in 3 ml of DMF together with 118 mg of propanesultone and 70 mg of potassium bicarbonate at 100° C. for 5 hours. To cleave the ester, the gellike mixture is admixed with 20 ml of 3M HCl and refluxed for 1 hour. Neutralization with sodium bicarbonate is followed by purification via RP chromatography.

Yield: 110 mg (28%) ($C_{21}H_{21}Cl_3N_2O_7S$, 551.83 g/mol)
MS ESI+(m/z): 551 (base, [M+H]$^-$), 553 (80%, [M+H]$^-$), 555 (40%, [M+H]$^-$)
UV-Vis in PBS: $\lambda_{max}$: 345 nm, $\lambda_{em}$: 506 nm, c=20.000 l/mol*cm, QY: 0.14

Working Example 4

1-(5-Carboxypentyl)-3-chloro-4-[6-(3-sulfonatopropoxy)benzooxazol-2-yl)pyridinium betaine Precursor 1:
2-(3-Chloropyridin-4-yl)benzooxazol-6-ol

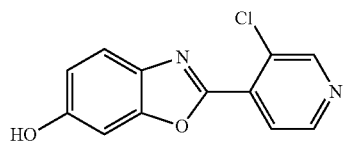 [SMILES: Oc1ccc2nc(-c3ccncc3Cl)oc2c1]

2.0 g of 4-aminoresorcinol hydrochloride, 1.95 g of 3-chloropyridine-4-carboxylic acid and 5 g of trimethylsilyl polyphosphate are heated in 20 ml of 1,2-dichlorobenzene and 2.11 ml of ethyldiisopropylamine to 180° C. for 6 hours. Cooling is followed by suspending with 70 ml of dichloromethane and neutralizing by admixture of 50 ml of 1N NaOH solution. This is followed by treatment in an ultrasonication bath until there is a pale gray fine precipitate, which is filtered, washed with a little water and dried. Yield: 910 mg (30%) ($C_{12}H_7ClN_2O_2$, 246.65 g/mol)

MS ESI–(m/z): 245 (base, [M–H])

Precursor 2: 3-Chloro-1-(5-ethoxycarbonylpentyl)-4-(6-hydroxybenzooxazol-2-yl)pyridinium bromide

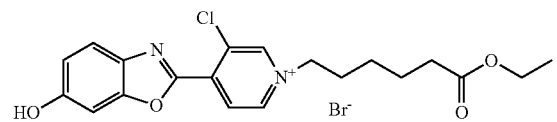

520 mg of precursor 1 are stirred with 500 mg of ethyl 6-bromohexanoate in 8 ml of DMF at 150° C. for 24 hours. After cooling, 40 ml of diethyl ether is added to bring down an oil, which is discarded. The organic solvent is distilled off and the residue is purified by RP chromatography.

Yield: 590 mg (60%) ($C_{20}H_{22}ClN_2O_4{}^+Br^-$, 469.76 g/mol)
MS ESI–(m/z): 387 (base, [M–H]$^-$)

Precursor 3: 1-(5-Carboxypentyl)-3-chloro-4-(6-hydroxybenzooxazol-2-yl)pyridinium bromide

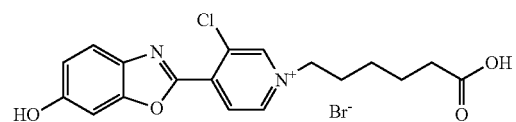 [SMILES: O=C(O)CCCCC[n+]1ccc(-c2nc3ccc(O)cc3o2)c(Cl)c1 ; [Br-]]

570 mg of precursor 2 are refluxed in 3M HCl for 1 hour. After cooling, the solution is neutralized with sodium bicarbonate. Purification is by RP chromatography.

Yield: 430 mg (80%) ($C_{18}H_{18}ClN_2O_4{}^+Br^-$, 441.71 g/mol)
MS ESI+(m/z): 361 (base, [M]$^+$)
UV-Vis in PBS: $\lambda_{max}$: 465 nm, $\lambda_{em}$: 655 nm, c=18.900 l/mol*cm, QY: 0.02
Compound 4:

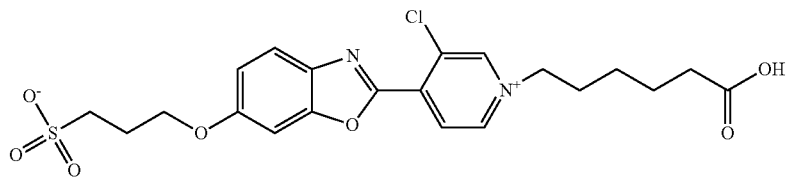 [SMILES: O=C(O)CCCCC[n+]1ccc(-c2nc3ccc(OCCCS(=O)(=O)[O-])cc3o2)c(Cl)c1]

325 mg of precursor 3 are stirred in 3 ml of DMF together with 118 mg of propanesultone and 70 mg of potassium bicarbonate at 100° C. for 5 hours. To cleave the ester, the gellike mixture is admixed with 20 ml of 3M HCl and refluxed for 1 hour. Neutralization with sodium bicarbonate is followed by purification via RP chromatography.

Yield: 140 mg (40%) ($C_{21}H_{23}ClN_2O_7S$, 482.94 g/mol)
MS ESI+(m/z): 483 (base, [M+H]$^+$), 485 (30%, [M+H $^{37}$Cl]$^+$)
UV-Vis in PBS: $\lambda_{max}$: 375 nm, $\lambda_{em}$: 510 nm, c=21.800 l/mol*cm; QY: 0.85

Working Example 5

1-(5-Carboxypentyl)-3-chloro-4-[5-sulfonato-6-(3-sulfonatopropoxy)benzooxazol-2-yl]pyridinium sodium salt

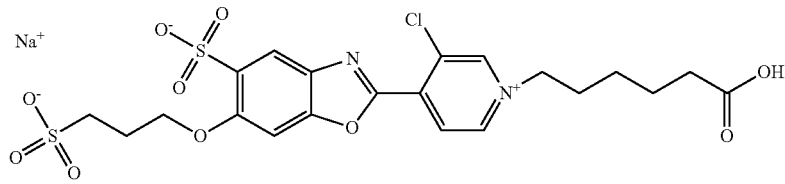 [SMILES: O=C(O)CCCCC[n+]1ccc(-c2nc3cc(S(=O)(=O)[O-])c(OCCCS(=O)(=O)[O-])cc3o2)c(Cl)c1 ; [Na+]]

120 mg of compound 4 are dissolved in 2 ml of 20% oleum, followed by stirring at 60° C. for 24 hours. The mixture is poured onto ice and the resultant solution is neutralized with sodium bicarbonate. Purification is by RP chromatography.

Yield: 60 mg (41%) ($C_{21}H_{22}ClN_2O_{10}S_2Na$, 584.99 g/mol)

MS ESI−(m/z): 561 (base, [M]$^-$)

UV-Vis in PBS: $\lambda_{max}$: 365 nm, $\lambda_{em}$: 495 nm, c=21.000 l/mol*cm, QY: 0.85

Working Example 6

1-[2-(2-{2-[2-(2-Carboxyethoxy)ethoxy]ethoxy}ethoxy)ethyl]-2-[6-(2-{2-[2-(2-methoxyethoxy)-ethoxy]ethoxy}ethoxy)benzooxazol-2-yl]pyridinium chloride Precursor 1: 2-Pyridin-2-ylbenzooxazol-6-ol

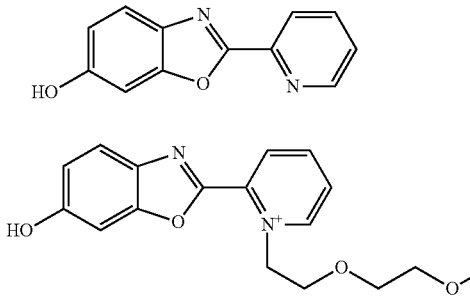

2.0 g of 4-aminoresorcinol hydrochloride, 1.52 g of pyridine-2-carboxylic acid and 5 g of trimethylsilyl polyphosphate are heated in 20 ml of 1,2-dichlorobenzene and 2.11 ml of ethyldiisopropylamine to 180° C. for 6 hours. Cooling is followed by suspending with 70 ml of dichloromethane and neutralizing by admixture of 50 ml of 1N NaOH solution. This is followed by treatment in an ultrasonication bath until there is a pale gray fine precipitate, which is filtered, washed with a little water and dried. Yield: 745 mg (28%) ($C_{12}H_8N_2O_2$, 212.21 g/mol)

MS ESI−(m/z): 211 (base, [M−H]$^-$)

Precursor 2: 1-[2-(2-{2-[2-(2-Carboxyethoxy)ethoxy]ethoxy}ethoxy)ethyl]-2-(6-hydroxybenzooxazol-2-yl)pyridinium toluenesulfonate 445 mg of precursor 1 are stirred with 1.1 g of tert-butyl 3-[2-(2-{2-[2-(toluene-4-sulfonyloxy)-ethoxy]ethoxy}ethoxy)ethoxy]propionate in 12 ml of DMF at 150° C. for 24 hours. The solvent is distilled off, the residue is repeatedly digested with heptanes and the supernatant solvent is discarded. The oily residue is purified by RP chromatography.

Yield: 570 mg (43%) ($C_{23}H_{29}N_2O_8^+C_7H_7O_3S^-$, 632.70 g/mol)

MS ESI+(m/z): 461 (base, [M]$^+$)

UV-Vis in PBS: $\lambda_{max}$: 372 nm, $\lambda_{em}$: 515 nm, c=18.500 l/mol*cm, QY: 0.02

Compound 6:

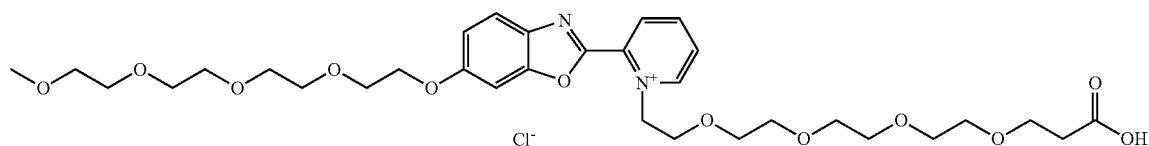 [SMILES: COCCOCCOCCOCCOc1ccc2nc(-c3cccc[n+]3CCOCCOCCOCCOCCC(=O)O)oc2c1 ; [Cl-]]

450 mg of precursor 2 are stirred in 5 ml of DMF together with 300 mg of 1-bromo-2-{2-[2-(2-methoxyethoxy)ethoxy]ethoxy}ethane and 70 mg of potassium bicarbonate at 100° C. for 16 hours. To cleave the ester, the mixture is admixed with 20 ml of 3M HCl and refluxed for 1 hour. Neutralization with sodium bicarbonate is followed by purification via RP chromatography.

Yield: 180 mg (37%) ($C_{32}H_{47}N_2O_{12}{}^+Cl^-$, 687.19 g/mol)
MS ESI+(m/z): 651 (base, [M]$^+$)

UV-Vis in PBS: $\lambda_{max}$: 375 nm, $\lambda_{em}$: 500 nm, c=20.200 l/mol*cm, QY: 0.72

Working Example 7

1-(5-Carboxypentyl)-4-[6-(5-carboxypentyloxyl)benzooxazol-2-yl]pyridinium betaine Precursor: 2-Pyridin-4-ylbenzooxazol-6-ol

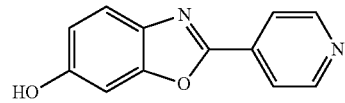 [SMILES: Oc1ccc2nc(-c3ccncc3)oc2c1]

2.0 g of 4-aminoresorcinol hydrochloride, 1.52 g of isonicotinic acid and 5 g of trimethylsilyl polyphosphate are heated in 20 ml of 1,2-dichlorobenzene and 2.11 ml of ethyldiisopropylamine to 180° C. for 6 hours. Cooling is followed by suspending with 70 ml of dichloromethane and neutralizing by admixture of 50 ml of 1N NaOH solution. This is followed by treatment in an ultrasonication bath until there is a pale gray fine precipitate, which is filtered, washed with a little water and dried. Yield: 745 mg (28%) ($C_{12}H_8N_2O_2$, 212.21 g/mol)
MS ESI−(m/z): 211 (base, [M−H]$^-$)
Compound 7:

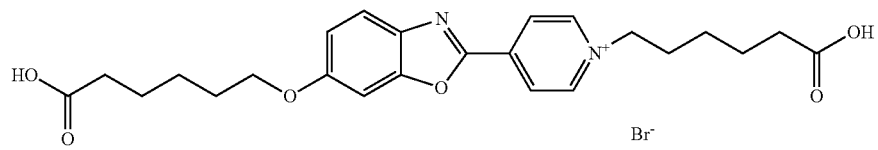 [SMILES: O=C(O)CCCCCOc1ccc2nc(-c3cc[n+](CCCCCC(=O)O)cc3)oc2c1 ; [Br-]]

500 mg of precursor are stirred in 8 ml of DMF with 1.6 g of ethyl 6-bromohexanoate and 235 mg of potassium bicarbonate at 100° C. for 5 hours and at 150° C. for 16 hours. The organic solvent is distilled off, the oily mixture is admixed with 30 ml of 3M HCl and refluxed for 1 hour. Neutralization with sodium bicarbonate is followed by purification via RP chromatography.

Yield: 710 mg (58%) ($C_{24}H_{29}N_2O_6{}^+Br^-$, 521.41 g/mol)
MS ESI+(m/z): 441 (base, [M]$^+$)
MS ESI−(m/z): 439 (base, [M−2H]$^-$)
UV-Vis in PBS: $\lambda_{max}$: 383 nm, $\lambda_{em}$: 516 nm, c=22.000 l/mol*cm, QY: 0.70

Working Example 8

1-(5-Carboxypentyl)-4-[6-(5-carboxypentyloxy)-5-sulfonatobenzooxazol-2-yl]pyridinium betaine

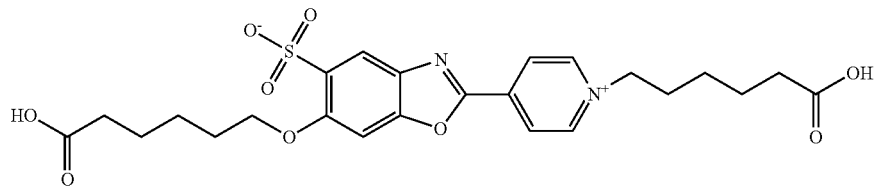 [SMILES: O=C(O)CCCCCOc1cc2oc(-c3cc[n+](CCCCCC(=O)O)cc3)nc2cc1S(=O)(=O)[O-]]

500 mg of compound 7 are dissolved in 3 ml of 20% oleum, followed by stirring at 60° C. for 24 hours. The mixture is poured onto ice and the resultant solution is neutralized with sodium bicarbonate. Purification is by RP chromatography.
Yield: 260 mg (52%) ($C_{24}H_{28}N_2O_9S$, 520.56 g/mol)
MS ESI−(m/z): 519 (base, [M−H]$^-$)
UV-Vis in PBS: $\lambda_{max}$: 370 nm, $\lambda_{em}$: 497 nm, c=20.700 l/mol*cm, QY: 0.69

Working Example 9

1-(5-Carboxypentyl)-4-[6-(3-sulfonatopropoxy)benzooxazol-2-yl]quinolinium betaine Precursor 1: 2-Quinolin-4-ylbenzooxazol-6-ol

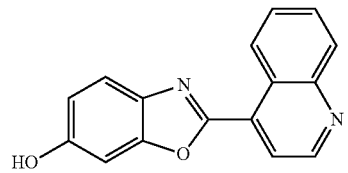 [SMILES: Oc1ccc2nc(-c3ccnc4ccccc34)oc2c1]

0.933 g of 4-aminoresorcinol hydrochloride, 1.0 g of 4-quinolinecarboxylic acid and 4 g of trimethylsilyl polyphosphate are heated in 10 ml of 1,2-dichlorobenzene and 0.99 ml of ethyldiisopropylamine to 180° C. for 6 hours. Cooling is followed by suspending with 70 ml of dichloromethane and neutralizing by admixture of 40 ml of 1N NaOH solution. This is followed by treatment in an ultrasonication bath until there is a pale gray fine precipitate, which is filtered, washed with a little water and a little dichloromethane and dried.

Yield: 595 mg (39%) ($C_{16}H_{10}N_2O_2$, 262.27 g/mol)
MS ESI–(m/z): 261 (base, [M–H]$^-$)

Precursor 2: 3-(2-Quinolin-4-ylbenzooxazol-6-yloxy)propane-1-sulfonic acid sodium salt

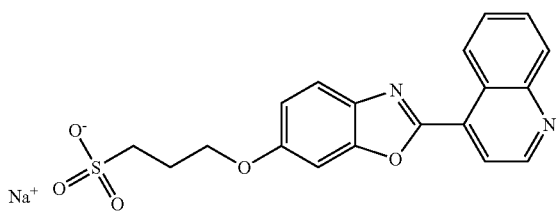 [SMILES: [Na+] ; O=S(=O)([O-])CCCOc1ccc2nc(-c3ccnc4ccccc34)oc2c1]

590 mg of precursor 1 are placed in 6 ml of dry DMF, admixed with 110 mg of sodium hydride (60% in mineral oil) a little at a time and stirred at RT for 30 minutes. Admixture of 412 mg of propanesultone is followed by stirring at 120° C. for 1 hour. The solvent is distilled off and the residue is treated with diethyl ether, bringing down a precipitate. It is filtered, washed with diethyl ether and dried.
Yield: 730 mg (80%) ($C_{19}H_{15}N_2O_5SNa$, 406.41 g/mol)
MS ESI–(m/z): 383 (base, [M]$^-$)
Compound 9:

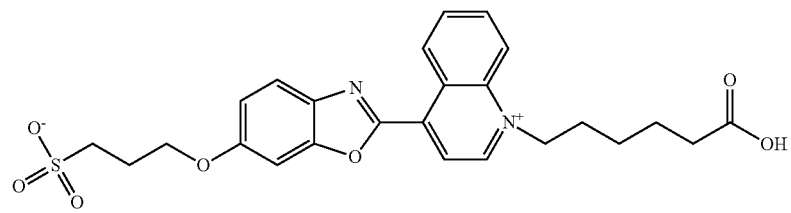 [SMILES: O=C(O)CCCCC[n+]1ccc(-c2nc3ccc(OCCCS(=O)(=O)[O-])cc3o2)c2ccccc21]

700 mg of precursor 2 are stirred with 450 mg of ethyl 6-bromohexanoate in 15 ml of DMF at 150° C. for 48 hours. After cooling, an oily precipitate is brought down with diethyl ether. To cleave the ester, said precipitate is refluxed in 20 ml of 3M HCl for 1 hour and cooled, and the solution is neutralized with sodium bicarbonate. Purification is by RP chromatography.
Yield: 435 mg (52%) ($C_{25}H_{26}N_2O_7S$, 498.56 g/mol)
MS ESI–(m/z): 497 (base, [M–H]$^-$)
UV-Vis in PBS: $\lambda_{max}$: 415 nm, $\lambda_{em}$: 568 nm, c=18.900 l/mol*cm, QY: 0.04

Working Example 10

1-(5-Carboxypentyl)-4-[5-sulfonato-6-(3-sulfonato-propoxy)benzooxazol-2-yl]quinolinium sodium salt 130 mg of compound 9 are dissolved in 2 ml of 20% oleum, followed by stirring at 60° C. for 24 hours. The mixture is poured onto ice and the resultant solution is neutralized with sodium bicarbonate. Purification is by RP chromatography.
Yield: 70 mg (47%) ($C_{25}H_{25}N_2O_{10}S_2Na$, 600.60 g/mol)
MS ESI–(m/z): 577 (base, [M]$^-$)
UV-Vis in PBS: $\lambda_{max}$: 403 nm, $\lambda_{em}$: 549 nm, c=18.000 l/mol*cm, QY: 0.15

Working Example 11

1-[2-(2-{2-[2-(2-Carboxyethoxy)ethoxy]ethoxy}ethoxy)ethyl]-2-[6-(3-sulfonato-propoxy)benzooxazol-2-yl]quinolinium betaine Precursor 1: 2-Quinolin-2-ylbenzooxazol-6-ol

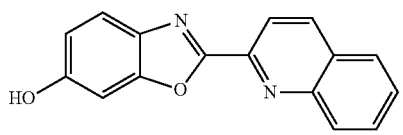

0.933 g of 4-aminoresorcinol hydrochloride, 1.0 g of quinoline-2-carboxylic acid and 4 g of trimethylsilyl polyphosphate are heated in 10 ml of 1,2-dichlorobenzene and 0.99 ml of ethyldiisopropylamine to 180° C. for 6 hours. Cooling is followed by suspending with 70 ml of dichloromethane and neutralizing by admixture of 40 ml of 1N NaOH solution. This is followed by treatment in an ultrasonication bath until there is a pale gray fine precipitate, which is filtered, washed with a little water and a little dichloromethane and dried.

Yield: 640 mg (42%) ($C_{16}H_{10}N_2O_2$, 262.27 g/mol)
MS ESI–(m/z): 261 (base, [M–H]$^-$)

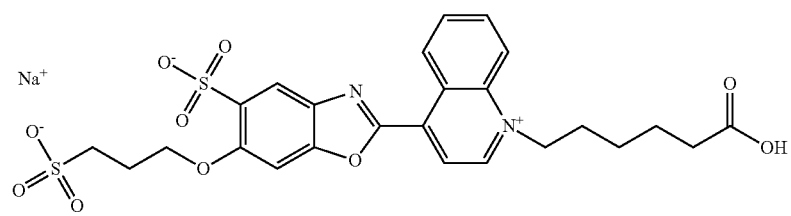 [SMILES: O=C(O)CCCCC[n+]1ccc(-c2nc3cc(S(=O)(=O)[O-])c(OCCCS(=O)(=O)[O-])cc3o2)c2ccccc21 ; [Na+]]

Precursor 2: 3-(2-Quinolin-2-ylbenzooxazol-6-yloxy)propane-1-sulfonic acid sodium salt

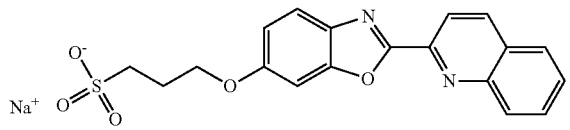 [SMILES: [Na+] ; O=S(=O)([O-])CCCOc1ccc2nc(-c3ccc4ccccc4n3)oc2c1]

590 mg of precursor 1 are placed in 6 ml of dry DMF, admixed with 110 mg of sodium hydride (60% in mineral oil) a little at a time and stirred at RT for 30 minutes. Admixture of 412 mg of propanesultone is followed by stirring at 120° C. for 1 hour. The solvent is distilled off and the residue is treated with diethyl ether, bringing down a precipitate. It is filtered, washed with diethyl ether and dried.

Yield: 690 mg (75%) ($C_{19}H_{15}N_2O_5SNa$, 406.41 g/mol)
MS ESI−(m/z): 383 (base, [M]⁻)
Compound 11:

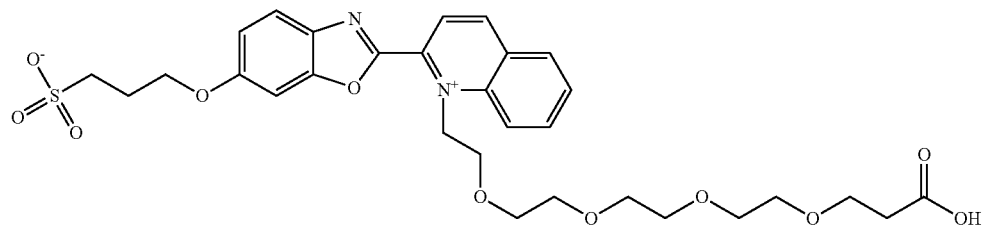 [SMILES: O=C(O)CCOCCOCCOCCOCC[n+]1c(-c2nc3ccc(OCCCS(=O)(=O)[O-])cc3o2)ccc2ccccc21]

600 mg of precursor 2 are stirred with 990 mg of tert-butyl 3-[2-(2-{2-[2-(toluene-4-sulfonyloxy)ethoxy]ethoxy}ethoxy)ethoxy]propionate in 15 ml of DMF at 150° C. for 48 hours.

The solvent is distilled off, the residue is repeatedly digested with heptanes and the supernatant solvent is discarded. The oily residue is purified by RP chromatography.

Yield: 360 mg (38%) ($C_{30}H_{36}N_2O_{11}S$, 632.69 g/mol)
MS ESI−(m/z): 631 (base, [M−H]⁻)
UV-Vis in PBS: $\lambda_{max}$: 405 nm, $\lambda_{em}$: 552 nm, c=18.200 l/mol*cm, QY: 0.06

Working Example 12

1-(5-Carboxypentyl)-4-(5-sulfonatonaphtho[1,2-d]oxazol-2-yl)quinolinium betaine

Precursor:
2-Quinolin-4-yl-naphtho[1,2-d]oxazole-5-sulfonic acid sodium salt

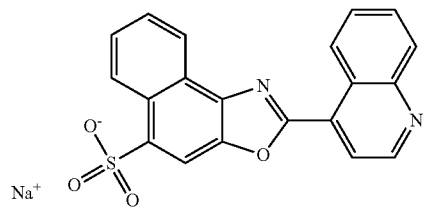 [SMILES: [Na+] ; O=S(=O)([O-])c1cc2oc(-c3ccnc4ccccc34)nc2c2ccccc12]

700 mg of 1-amino-2-naphthol-4-sulfonic acid sodium salt, 500 mg of quinoline-4-carboxylic acid and 2 g of trimethylsilyl polyphosphate are heated in 7 ml of 1,2-dichlorobenzene to 180° C. for 12 hours. Cooling is followed by suspending with 20 ml of dichloromethane and neutralizing by admixture of 20 ml of 1N NaOH solution. This is followed by treatment in an ultrasonication bath until the tacky precipitate has substantially dissolved. The aqueous phase is separated off and purified via RP chromatography.

Yield: 115 mg (10%) ($C_{20}H_{11}N_2O_4SNa$, 398.38 g/mol)
MS ESI−(m/z): 375 (base, [M]⁻)
Compound 12:

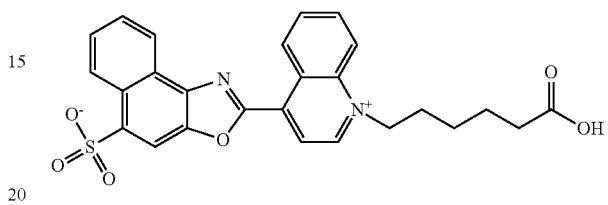

80 mg of precursor are stirred with 90 mg of ethyl 6-bromohexanoate in 5 ml of DMF at 150° C. for 48 hours. The solvent is distilled off and the residue is refluxed in 10 ml of 3M HCl for 1 hour. After cooling, the solution is neutralized with sodium bicarbonate. Purification is by RP chromatography.

Yield: 12 mg (12%) ($C_{26}H_{22}N_2O_6S$, 490.54 g/mol)
MS ESI−(m/z): 489 (base, [M−H]⁻)
UV-Vis in PBS: $\lambda_{max}$: 414 nm, $\lambda_{em}$: 555 nm, c=19.000 l/mol*cm, QY: 0.43

Working Example 13

1-(5-Carboxypentyl)-3-{2-[6-(3-sulfonatopropoxy)benzooxazol-2-yl]vinyl}pyridinium betaine Precursor 1:
2-(2-Pyridin-3-yl-vinyl)benzooxazol-6-ol

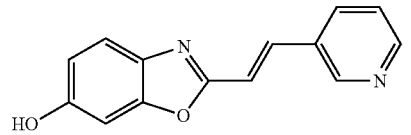 [SMILES: Oc1ccc2nc(/C=C/c3cccnc3)oc2c1]

2.0 g of 4-aminoresorcinol hydrochloride, 1.85 g of trans-3-(3-pyridyl)acrylic acid and 5 g of trimethylsilyl polyphosphate are heated in 20 ml of 1,2-dichlorobenzene and 2.11 ml of ethyldiisopropylamine to 180° C. for 6 hours. Cooling is followed by neutralizing with 50 ml of 1N NaOH solution. This is followed by treatment in an ultrasonication bath until there is a pale gray fine precipitate, which is filtered, washed with a little water and a little dichloromethane and dried. Yield: 830 mg (28%) ($C_{14}H_{10}N_2O_2$, 238.25 g/mol)

MS ESI−(m/z): 237 (base, [M−H]⁻)

UV-Vis in PBS: $\lambda_{max}$: 340 nm, $\lambda_{em}$: 455 nm, c=15.500 l/mol*cm, QY: 0.40

Precursor 2: 3-[2-(2-Pyridin-3-yl-vinyl)benzooxazol-6-yloxy]propane-1-sulfonic acid sodium salt

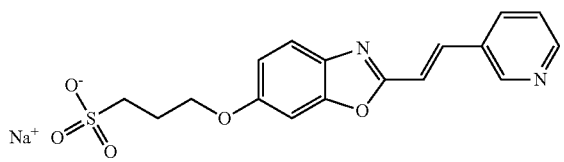 [SMILES: [Na+] ; O=S(=O)([O-])CCCOc1ccc2nc(/C=C/c3cccnc3)oc2c1]

800 mg of precursor 1 are placed in 30 ml of dry DMF, admixed with 150 mg of sodium hydride (60% in mineral oil) a little at a time and stirred at RT for 1 hour. Admixture of 420 mg of propanesultone is followed by stirring at 120° C. for 1 hour. After cooling, the precipitation is completed by admixture of diethyl ether. The precipitate is taken up in methanol and filtered, the solvent is distilled off and the residue is dried.

Yield: 1.1 g (80%) ($C_{17}H_{15}N_2O_5SNa$, 382.37 g/mol)

MS ESI−(m/z): 359 (base, [M]⁻)

UV-Vis in PBS: $\lambda_{max}$: 339 nm, $\lambda_{em}$: 445 nm, c=17.000 l/mol*cm, QY: 0.74

Compound 13:

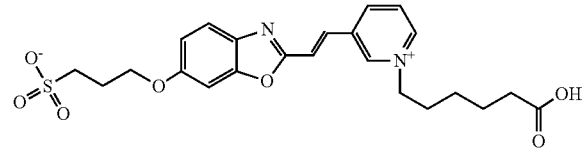 [SMILES: O=C(O)CCCCC[n+]1cccc(/C=C/c2nc3ccc(OCCCS(=O)(=O)[O-])cc3o2)c1]

600 mg of precursor 2 are stirred with 400 mg of ethyl 6-bromohexanoate in 20 ml of DMF at 150° C. for 8 hours. The solvent is distilled off and the residue is refluxed in 25 ml of 3M HCl for 1 hour. After cooling, the solution is neutralized with sodium bicarbonate. Purification is by RP chromatography.

Yield: 75 mg (10%) ($C_{23}H_{26}N_2O_7S$, 474.54 g/mol)

MS ESI−(m/z): 473 (base, [M−H]⁻)

UV-Vis in PBS: $\lambda_{max}$: 360 nm, $\lambda_{em}$: 530 nm, c=17.000 l/mol*cm, QY: 0.02

Working Example 14

1-(5-Carboxypentyl)-4-(6-methoxybenzooxazol-2-yl)pyridinium bromide Precursor: 6-Methoxy-2-pyridin-4-ylbenzooxazole

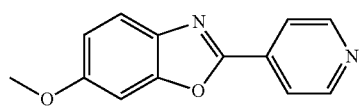 [SMILES: COc1ccc2nc(-c3ccncc3)oc2c1]

1.4 g of 2-amino-5-methoxyphenol, 1.25 g of isonicotinic acid and 10 g of trimethylsilyl polyphosphate are heated in 18 ml of 1,2-dichlorobenzene to 180° C. for 4 hours. Cooling is followed by suspending with 70 ml of dichloromethane and neutralizing by admixture of 100 ml of 1N NaOH solution. This is followed by treatment in an ultrasonication bath until there is a pale gray fine precipitate, which is filtered, washed with a little water and dried. Yield: 725 mg (32%)

($C_{13}H_{10}N_2O_2$, 226.24 g/mol)

MS ESI+(m/z): 227 (base, [M+H]⁺)

Compound 14:

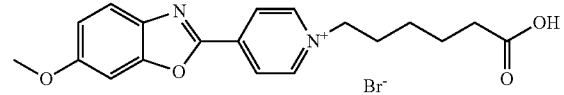 [SMILES: COc1ccc2nc(-c3cc[n+](CCCCCC(=O)O)cc3)oc2c1 ; [Br-]]

500 mg of precursor are stirred with 1 g of ethyl 6-bromohexanoate in 4 ml of 1,2-dichlorobenzene and 4 ml of DMF at 150° C. for 24 hours. After cooling, 100 ml of diethyl ether are added to bring down an oil which is refluxed in 10 ml of 3M HCl for 1 hour. After cooling, the solution is neutralized with sodium bicarbonate. Purification is by RP chromatography.

Yield: 130 mg (14%) ($C_{19}H_{21}N_2O_4^+Br^-$, 421.29 g/mol)

MS ESI+(m/z): 420 (base, [M]⁺)

UV-Vis in PBS: $\lambda_{max}$: 380 nm, $\lambda_{em}$: 511 nm, c=19.800 l/mol*cm, QY: 0.50

Working Example 15

1-(5-Carboxypentyl)-4-(6-methoxy-5-sulfonatobenzooxazol-2-yl)pyridinium betaine

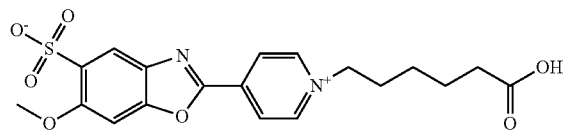 [SMILES: COc1cc2oc(-c3cc[n+](CCCCCC(=O)O)cc3)nc2cc1S(=O)(=O)[O-]]

100 mg of compound 14 are dissolved in 2 ml of 20% oleum, followed by stirring at RT for 2 hours. The mixture is poured onto ice and the resultant solution is neutralized with sodium bicarbonate. Purification is by RP chromatography.

Yield: 55 mg (54%) ($C_{19}H_{20}H_2O_7S$, 420.44 g/mol)

MS ESI−(m/z): 419 (base, [M−H]⁻)

UV-Vis in PBS: $\lambda_{max}$: 369 nm, $\lambda_{em}$: 495 nm, c=19.200 l/mol*cm, QY: 0.70

Working Example 16

1-(3-Hydroxypropyl)-4-(6-methoxybenzooxazol-2-yl)pyridinium bromide

Precursor: 6-Methoxy-2-pyridin-4-ylbenzooxazole

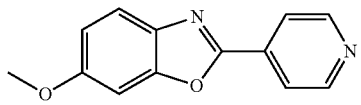 [SMILES: COc1ccc2nc(-c3ccncc3)oc2c1]

1.4 g of 2-amino-5-methoxyphenol, 1.25 g of isonicotinic acid and 10 g of trimethylsilyl polyphosphate are heated in 18 ml of 1,2-dichlorobenzene to 180° C. for 4 hours. Cooling is followed by suspending with 70 ml of dichloromethane and neutralizing by admixture of 100 ml of 1N NaOH solution. This is followed by treatment in an ultrasonication bath until there is a pale gray fine precipitate, which is filtered, washed with a little water and dried. Yield: 725 mg (32%)

($C_{13}H_{10}N_2O_2$, 226.24 g/mol)

MS ESI+(m/z): 227 (base, $[M+H]^+$)

Compound 16:

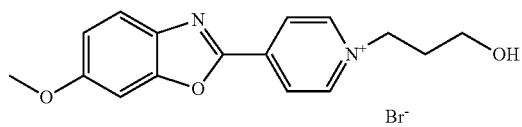 [SMILES: COc1ccc2nc(-c3cc[n+](CCCO)cc3)oc2c1 ; [Br-]]

500 mg of 2.21 mmol precursor are stirred with 800 mg of 3-bromopropyl acetate in 4 ml of 1,2-dichlorobenzene and 4 ml of DMF at 150° C. for 24 hours. After cooling, 100 ml of diethyl ether are added to bring down an oil which is refluxed in 10 ml of 3M HCl for 1 hour. After cooling, the solution is neutralized with sodium bicarbonate. Purification is by RP chromatography.

Yield: 130 mg (16%) ($C_{16}H_{17}N_2O_3{}^+Br^-$, 365.22 g/mol)

MS ESI+(m/z): 285 (base, $[M]^+$)

UV-Vis in PBS: $\lambda_{max}$: 379 nm, $\lambda_{em}$: 510 nm, c=20.000 l/mol*cm, QY: 0.50

Working Example 17

4-[6-(4-Carboxybutyrylamino)benzooxazol-2-yl]-1-(3-sulfonatopropyl)pyridinium betaine Precursor: 4-(2-Pyridin-4-ylbenzooxazol-6-ylcarbamoyl)butyric acid

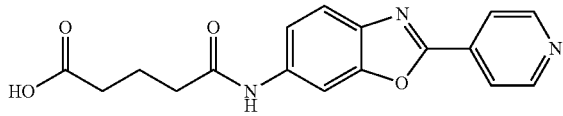 [SMILES: O=C(O)CCCC(=O)Nc1ccc2nc(-c3ccncc3)oc2c1]

2.5 g of 4-(4-amino-3-hydroxyphenylcarbamoyl)butyric acid, 1.3 g of isonicotinic acid and 10 g of trimethylsilyl polyphosphate are heated in 18 ml of 1,2-dichlorobenzene to 180° C. for 4 hours. Cooling is followed by suspending with 70 ml of dichloromethane and neutralizing by admixture of 100 ml of 1N NaOH solution. This is followed by treatment in an ultrasonication bath until there is a pale gray fine precipitate, which is filtered, washed with a little water and dried.

Yield: 750 mg (22%) ($C_{17}H_{15}N_3O_4$, 325.33 g/mol)

MS ESI-(m/z): 324 (base, $[M-H]^-$)

Compound 17:

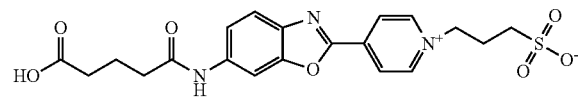

500 mg of precursor are stirred with 375 mg of propanesultone in 4 ml of DMF at 120° C. for 8 hours. The solvent is distilled off and the residue is purified using RP chromatography.

Yield: 330 mg (48%) ($C_{20}H_{21}N_3O_7S$, 447.47 g/mol)

MS ESI-(m/z): 446 (base, $[M-H]^-$)

UV-Vis in PBS: $\lambda_{max}$: 375 nm, $\lambda_{em}$: 543 nm (cf. FIG. 4), c=16.000 l/mol*cm, QY: 0.62

Working Example 18

1-(5-Carboxypentyl)-4-(6-ethoxycarbonylaminobenzooxazol-2-yl)pyridinium bromide

Precursor: Ethyl (2-pyridin-4-ylbenzooxazol-6-yl)carbamate

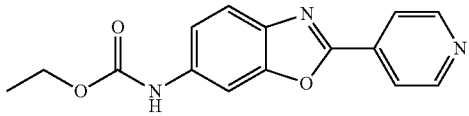 [SMILES: CCOC(=O)Nc1ccc2nc(-c3ccncc3)oc2c1]

2.0 g of ethyl (4-amino-3-hydroxyphenyl)carbamate, 1.3 g of isonicotinic acid and 10 g of trimethylsilyl polyphosphate are heated in 18 ml of 1,2-dichlorobenzene to 180° C. for 4 hours. Cooling is followed by suspending with 50 ml of dichloromethane and neutralizing by admixture of 100 ml of 1N NaOH solution. This is followed by treatment in an ultrasonication bath until there is a pale gray fine precipitate, which is filtered, washed with a little water and dried.

Yield: 340 mg (12%) ($C_{15}H_{13}N_3O_3$, 283.29 g/mol)

MS ESI+(m/z): 284 (base, $[M+H]^+$)

Compound 18:

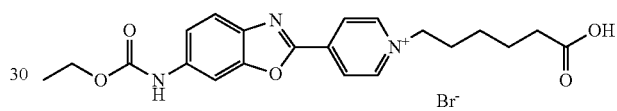

340 mg of precursor are stirred with 530 mg of ethyl 6-bromohexanoate in 3 ml of 1,2-dichlorobenzene and 3 ml of DMF at 150° C. for 24 hours. After cooling, 100 ml of diethyl ether are added to bring down an oil, which is stirred in a mixture of 30 ml of acetone and 20 ml of concentrated sodium bicarbonate solution at 50° C. for 4 hours. The mixture is neutralized with 5% HBr. Purification is by RP chromatography.

Yield: 80 mg (14%) ($C_{21}H_{24}N_3O_5{}^+Br^-$, 478.34 g/mol)

MS ESI+(m/z): 398 (base, $[M]^+$)

UV-Vis in PBS: $\lambda_{max}$: 383 nm, $\lambda_{em}$: 543 nm, c=17.000 l/mol*cm, QY: 0.54

Working Example 19

4-{6-[3-(5-Carboxypentyl)ureido]benzooxazol-2-yl}-1-(3-sulfonatopropyl)pyridinium betaine Precursor: 6-[3-(2-Pyridin-4-ylbenzooxazol-6-yl)ureido]hexanoic acid

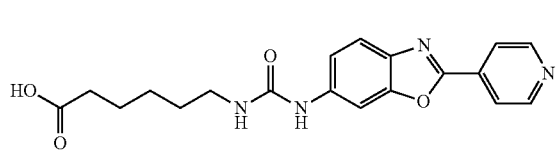 [SMILES: O=C(O)CCCCCNC(=O)Nc1ccc2nc(-c3ccncc3)oc2c1]

4.0 g of 6-[3-(4-amino-3-hydroxyphenyl)ureido]hexanoic acid, 1.75 g of isonicotinic acid and 13 g of trimethylsilyl polyphosphate are heated in 20 ml of 1,2-dichlorobenzene to 180° C. for 4 hours. Cooling is followed by suspending with 70 ml of dichloromethane and neutralizing by admixture of 120 ml of 1N NaOH solution. This is followed by treatment in an ultrasonication bath until there is a pale gray fine precipitate, which is filtered, washed with a little water and dried.

Yield: 420 mg (8%) ($C_{19}H_{20}N_4O_4$, 368.40 g/mol)

MS ESI−(m/z): 367 (base, [M−H]⁻)

Compound 19:

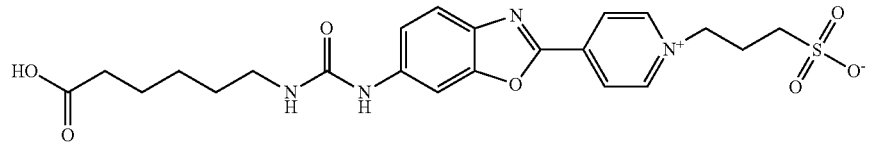 [SMILES: O=C(O)CCCCCNC(=O)Nc1ccc2nc(-c3cc[n+](CCCS(=O)(=O)[O-])cc3)oc2c1]

400 mg of precursor are stirred with 265 mg of propanesultone in 4 ml of DMF at 120° C. for 8 hours. The solvent is distilled off and the residue is purified using RP chromatography.

Yield: 195 mg (37%) ($C_{22}H_{26}N_4O_7S$, 490.54 g/mol)

MS ESI−(m/z): 489 (base, [M]⁺)

UV-Vis in PBS: $\lambda_{max}$: 397 nm, $\lambda_{em}$: 572 nm (cf. FIG. 5), c=20.000 l/mol*cm; QY: 0.28

Working Example 20

4-{6-[Bis-(3-sulfonatopropyl)amino]benzooxazol-2-yl}-1-(5-carboxypentyl)pyridinium sodium salt Precursor: 3-[(2-Pyridin-4-yl-benzooxazol-6-yl)-(3-sulfonatopropyl)amino]propanesulfonic acid disodium salt

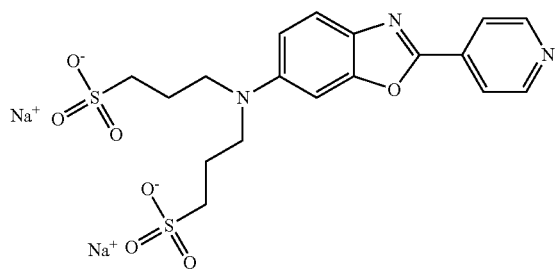 [SMILES: [Na+] ; O=S(=O)([O-])CCCN(CCCS(=O)(=O)[O-])c1ccc2nc(-c3ccncc3)oc2c1 ; [Na+]]

2.0 g of 3-[(4-amino-3-hydroxyphenyl)-(3-sulfonatopropyl)amino]propanesufonic acid disodium salt, 600 mg of isonicotinic acid and 6 g of trimethylsilyl polyphosphate are heated in 15 ml of 1,2-dichlorobenzene to 180° C. for 4 hours. After cooling, the mixture is diluted with 50 ml of dichloromethane and neutralized by admixture of 65 ml of 1N NaOH solution. This is followed by treatment in an ultrasonication bath until the tacky precipitate has substantially dissolved. The aqueous phase is separated off and purified via RP chromatography.

Yield: 675 mg (28%) ($C_{18}H_{19}N_3O_7S_2Na_2$, 499.48 g/mol)

MS ESI−(m/z): 226.7 (base, [M]²⁻)

Compound 20:

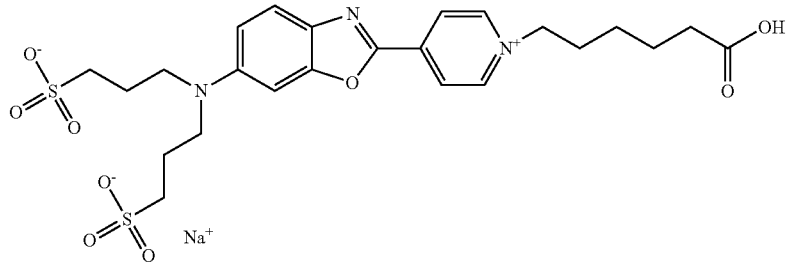 [SMILES: O=C(O)CCCCC[n+]1ccc(-c2nc3ccc(N(CCCS(=O)(=O)[O-])CCCS(=O)(=O)[O-])cc3o2)cc1 ; [Na+]]

500 mg of precursor are stirred with 450 mg of ethyl 6-bromohexanoate in 3 ml of 1,2-dichlorobenzene and 5 ml of DMF at 150° C. for 24 hours. After cooling, 50 ml of diethyl ether are added to bring down an oil which is refluxed in 10 ml of 3M HCl for 1 hour. After cooling, the solution is neutralized with sodium bicarbonate. Purification is by RP chromatography.

Yield: 115 mg (19%) ($C_{24}H_{30}N_3O_9S_2Na$, 591.64 g/mol)

MS ESI−(m/z): 568 (base, [M]⁻)

UV-Vis in PBS: $\lambda_{max}$: 491 nm, $\lambda_{em}$: 666 nm, c=17.700 l/mol*cm, QY: 0.06

Working Example 21

4-{6-[1-(3-Sulfonatopropyl)-3-(5-carboxypentyl)ureido]benzooxazol-2-yl}-1-(3-sulfonatopropyl)pyridinium disodium salt Precursor: 4-{6-[1-(3-Sulfonatopropyl)-3-(5-carboxypentyl)ureido]benzooxazol-2-yl}pyridine sodium salt

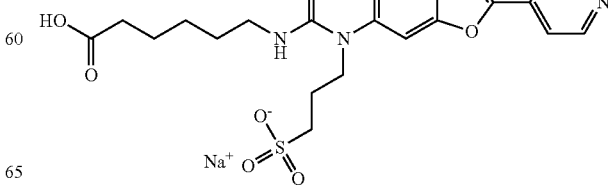

5.0 g of 6-[3-(4-Amino-3-hydroxyphenyl)ureido]hexanoic acid, 2.1 g of isonicotinic acid and 15 g of trimethylsilyl polyphosphate are heated in 25 ml of 1,2-dichlorobenzene to 180° C. for 4 hours. After cooling, the mixture is suspended with 70 ml of dichloromethane and neutralized by admixture of 120 ml of 1N NaOH solution. This is followed by treatment in an ultrasonication bath until the tacky precipitate has substantially dissolved. The aqueous phase is separated off and purified via RP chromatography.

Yield: 660 mg (11%) ($C_{22}H_{25}N_4O_7SNa$, 512.52 g/mol)
MS ESI–(m/z): 489 (base, [M]$^-$)

Compound 21:

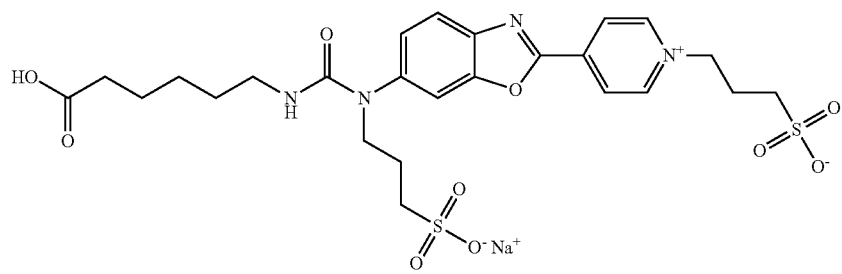

660 mg of precursor are stirred with 300 mg of propanesultone in 8 ml of DMF at 120° C. for 8 hours. The solvent is distilled off and the residue is purified using RP chromatography.

Yield: 280 mg (33%) ($C_{25}H_{31}N_4O_{10}S_2Na$, 634.66 g/mol)
MS ESI–(m/z): 611 (base, [M+Na]$^-$)
UV-Vis in PBS: $\Delta\lambda_{max}$: 353 nm, $\lambda_{em}$: 614 nm (cf. FIG. 6), c=16.000 l/mol*cm, QY: 0.29

Working Example 22

1-(5-Carboxypentyl)-4-(4,7-disulfonatonaphtho[1,2-d]oxazol-2-yl)pyridinium sodium salt Precursor:
2-Pyridin-4-yl-naphtho[1,2-d]oxazol-4,7-disulfonic acid disodium salt

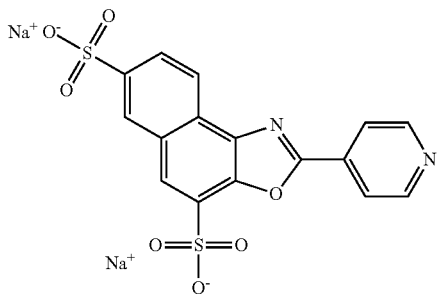

3.6 g of 4-amino-3-hydroxynaphthalene-2,7-disulfonic acid disodium salt, 1.22 g of isonicotinic acid and 10 g of trimethylsilyl polyphosphate are heated in 18 ml of 1,2-dichlorobenzene to 180° C. for 4 hours. After cooling, the mixture is diluted with 50 ml of dichloromethane and neutralized by admixture of 100 ml of 1N NaOH solution. This is followed by treatment in an ultrasonication bath until the tacky precipitate has substantially dissolved. The aqueous phase is separated off and purified via RP chromatography.

Yield: 735 mg (16%) ($C_{16}H_8N_2O_7S_2Na_2$, 450.36 g/mol)
MS ESI–(m/z): 202 (base, [M]$^{2-}$)

Compound 22:

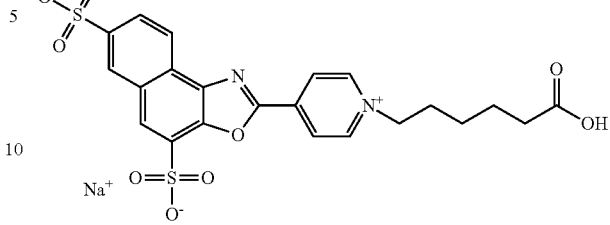

600 mg of precursor are stirred with 600 mg of ethyl 6-bromohexanoate in 3 ml of 1,2-dichlorobenzene and 5 ml of DMF at 150° C. for 24 hours. After cooling, 50 ml of diethyl ether are added to bring down an oil which is refluxed in 10 ml of 3M HCl for 1 hour. After cooling, the solution is neutralized with sodium bicarbonate. Purification is by RP chromatography.

Yield: 80 mg (11%) ($C_{22}H_{19}N_2O_9S_2Na$, 542.52 g/mol)
MS ESI–(m/z): 520 (base, [M]$^-$)
UV-Vis in PBS: $\lambda_{max}$: 376 nm, $\lambda_{em}$: 484 nm (cf. FIG. 2), c=15.700 l/mol*cm, QY: 0.75

Working Example 23

1-(5-Carboxypentyl)-2-(4,7-disulfonatonaphtho[1,2-d]oxazol-2-yl)quinolinium sodium salt Precursor: 2-Quinolin-2-yl-naphtho[1,2-d]oxazole-4,7-disulfonic acid disodium salt

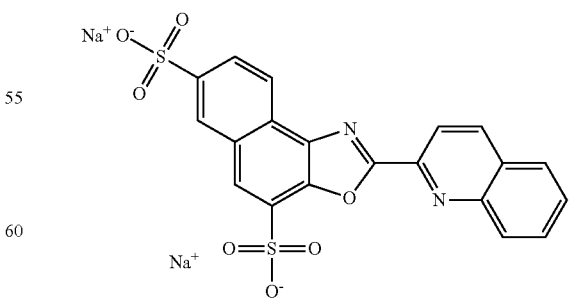

1 g of 4-amino-3-hydroxynaphthalene-2,7-disulfonic acid disodium salt, 480 mg of quinoline-2-carboxylic acid and 4.0 g of trimethylsilyl polyphosphate are heated in 6 ml of 1,2-dichlorobenzene to 180° C. for 9 hours. Cooling is followed by suspending with 20 ml of dichloromethane and neutralizing by admixture of 40 ml of 1N NaOH solution. The aqueous phase is separated off and purified via RP chromatography.

Yield: 250 mg (18%) ($C_{20}H_{10}N_2O_7S_2Na_2$, 500.42 g/mol)

MS ESI−(m/z): 227 (base, $[M]^{2-}$)

Compound 23:

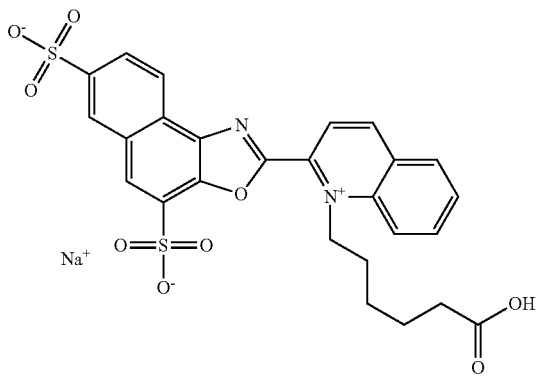 [SMILES: O=C(O)CCCCC[n+]1c(-c2nc3c(o2)c(S(=O)(=O)[O-])cc2cc(S(=O)(=O)[O-])ccc23)ccc2ccccc21 ; [Na+]]

190 mg of precursor are stirred with 170 mg of ethyl 6-bromohexanoate in 2 ml of DMF at 150° C. for 48 hours. The solvent is distilled off and the residue is refluxed in 5 ml 3M HCl for 1 hour. After cooling, the solution is neutralized with sodium bicarbonate. Purification is by RP chromatography.

Yield: 36 mg (16%) ($C_{26}H_{21}N_2O_9S_2Na$, 592.58 g/mol)

MS ESI−(m/z): 569 (base, $[M]^-$)

UV-Vis in PBS: $\lambda_{max}$: 494 nm, $\lambda_{em}$: 515 nm, c=18.000 l/mol*cm, QY: 0.75

Working Example 24

1-(5-Carboxypentyl)-4-(4,7-disulfonatonaphtho[1,2-d]oxazol-2-yl)quinolinium sodium salt Precursor: 2-Quinolin-4-ylnaphtho[1,2-d]oxazole-4,7-disulfonic acid disodium salt

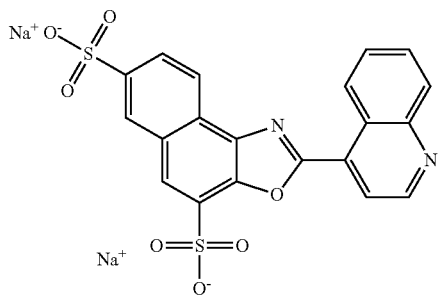

1 g of 4-amino-3-hydroxynaphthalene-2,7-disulfonic acid disodium salt, 480 mg of quinoline-4-carboxylic acid and 4.0 g of trimethylsilyl polyphosphate are heated in 6 ml of 1,2-dichlorobenzene to 180° C. for 9 hours. Cooling is followed by suspending with 20 ml of dichloromethane and neutralizing by admixture of 40 ml of 1N NaOH solution. The aqueous phase is separated off and purified via RP chromatography.

Yield: 205 mg (15%) ($C_{20}H_{10}N_2O_7S_2Na_2$, 500.42 g/mol)

MS ESI−(m/z): 227 (base, $[M]^{2-}$)

Compound 24:

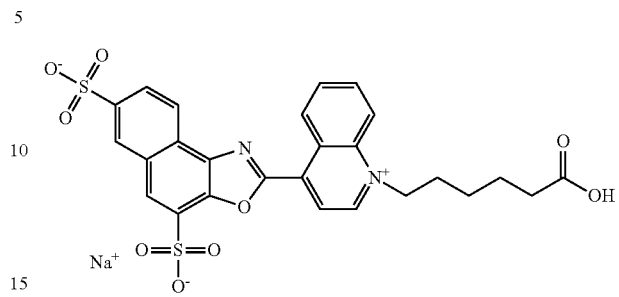

190 mg of precursor are stirred with 170 mg of ethyl 6-bromohexanoate in 2 ml of DMF at 150° C. for 48 hours. The solvent is distilled off and the residue is refluxed in 5 ml 3M HCl for 1 hour. After cooling, the solution is neutralized with sodium bicarbonate. Purification is by RP chromatography.

Yield: 31 mg (14%) ($C_{26}H_{21}N_2O_9S_2Na$, 592.58 g/mol)

MS ESI−(m/z): 569 (base, $[M]^-$)

UV-Vis in PBS: $\lambda_{max}$: 404 nm, $\lambda_{em}$: 535 nm, c=18.000 l/mol*cm, QY: 0.73

Working Example 25

1-(5-Carboxypentyl)-2-(4,7-disulfonatonaphtho[1,2-d]oxazol-2-yl)pyridinium sodium salt Precursor: 2-Pyridin-2-ylnaphtho[1,2-d]oxazole-4,7-disulfonic acid disodium salt

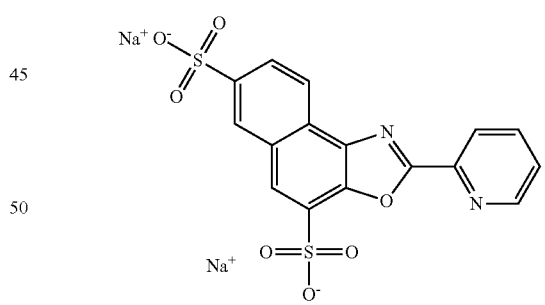

5 g of 4-amino-3-hydroxynaphthalene-2,7-disulfonic acid disodium salt, 1.7 g of 2-picolinic acid and 14 g of trimethylsilyl polyphosphate are heated in 22 ml of 1,2-dichlorobenzene to 180° C. for 4 hours. Cooling is followed by diluting with 70 ml of dichloromethane and neutralizing by admixture of 140 ml of 1N NaOH solution. This is followed by treatment in an ultrasonication bath until the tacky precipitate has substantially dissolved. The aqueous phase is separated off and purified via RP chromatography.

Yield: 740 mg (12%) ($C_{16}H_8N_2O_7S_2Na_2$, 450.36 g/mol)

MS ESI−(m/z): 202 (base, $[M]^{2-}$)

Compound 25:

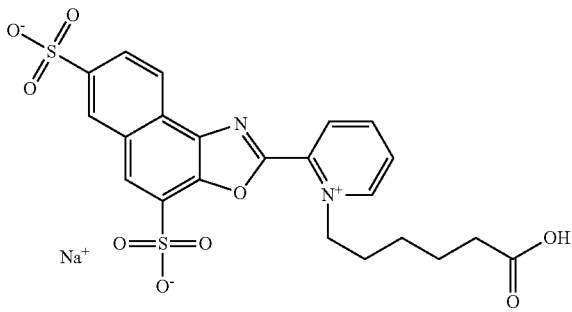 [SMILES: O=C(O)CCCCC[n+]1ccccc1-c1nc2c(o1)c(S(=O)(=O)[O-])cc1cc(S(=O)(=O)[O-])ccc12 ; [Na+]]

700 mg of precursor are stirred with 700 mg of ethyl 6-bromohexanoate in 4 ml of 1,2-dichlorobenzene and 6 ml of DMF (dimethylformamide) at 150° C. for 24 hours. After cooling, 70 ml of diethyl ether are added to bring down an oil which is refluxed in 15 ml of 3M HCl for 1 hour. After cooling, the solution is neutralized with sodium bicarbonate. Purification is by RP chromatography.

Yield: 75 mg (9%) ($C_{22}H_{19}N_2O_9S_2Na$, 542.52 g/mol)
MS ESI−(m/z): 520 (base, [M]⁻)

UV-Vis in PBS: $\lambda_{max}$: 368 nm, $\lambda_{em}$: 474 nm, c=13.200 l/mol*cm, QY: 0.85

Working ExampleS 26-49

NHS Esters

The NHS esters of the compounds obtained according to Working Examples 1 to 15 and 17 to 25 are prepared by the following method:

0.25 mmol of the carboxylic acid are dissolved in 3 ml of DMF. This is followed by the admixture at 0° C. of 90 mg of TSTU (N,N,N',N'-tetramethyl-O—(N-succinimidyl)uronium tetrafluoroborate) and 52 µl of DIPEA (diisopropylethylamine) and stirring at RT for 20 minutes. In the case of compound 7, 200 mg of TSTU and 120 µl of DIPEA are used. The solvent is distilled off in vacuo and the residue is purified via an RP column.

The table which follows is a line by line listing of the NHS esters (last column) obtained from a particular starting compound (second column) on using the method described above. The numbers 1 to 15 and 17 to 25 for the starting compounds correspond to the numbers for Working Examples 1 to 15 and 17 to 25.

| Working Example | Starting compound | Empirical formula | Molar mass [g/mol] | NHS ester |
|---|---|---|---|---|
| 26 | 1 | $C_{25}H_{27}N_3O_9S$ | 545.57 | |
| 27 | 2 | $C_{25}H_{26}ClN_3O_9S$ | 580.02 | |
| 28 | 3 | $C_{25}H_{24}Cl_3N_3O_9S$ | 648.91 | |
| 29 | 4 | $C_{25}H_{26}ClN_3O_9S$ | 580.02 | |
| 30 | 5 | $C_{25}H_{25}ClN_3O_{12}S_2Na$ | 682.06 | |

-continued
| Working Example | Starting compound | Empirical formula | Molar mass [g/mol] | NHS ester |
|---|---|---|---|---|
| 31 | 6 | $C_{36}H_{50}N_3O_{14}Cl$ | 784.26 | 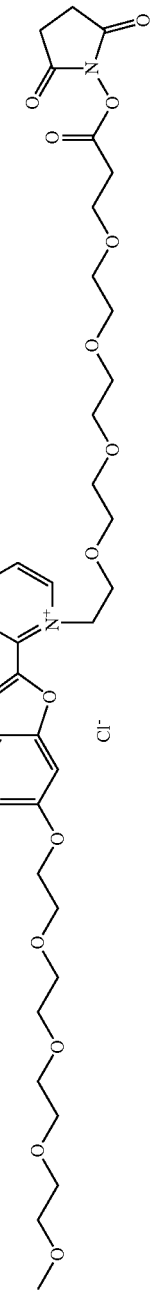 |
| 32 | 7 | $C_{32}H_{35}N_4O_{10}Br$ | 715.56 | 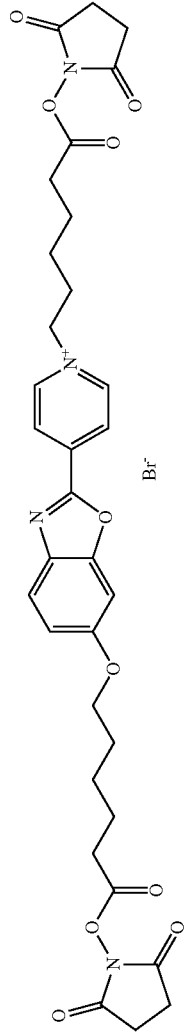 |
| 33 | 8 | $C_{32}H_{34}N_4O_{13}S$ | 714.71 | 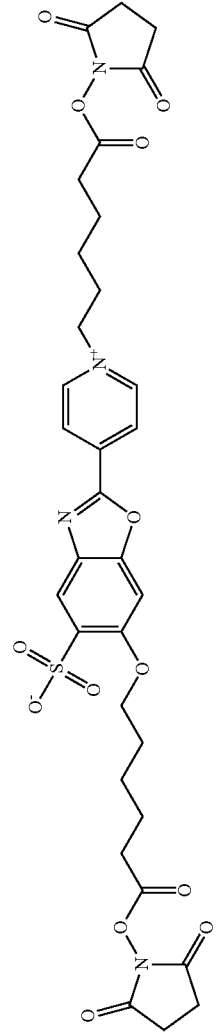 |
| 34 | 9 | $C_{29}H_{29}N_3O_9S$ | 595.63 | 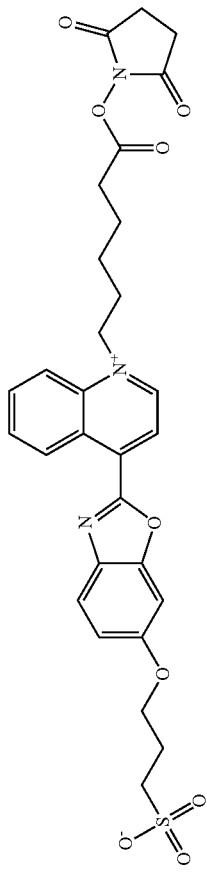 |

-continued
| Working Example | Starting compound | Empirical formula | Molar mass [g/mol] | NHS ester |
|---|---|---|---|---|
| 35 | 10 | $C_{29}H_{28}N_3O_{12}S_2Na$ | 697.68 | |
| 36 | 11 | $C_{34}H_{39}N_3O_{13}S$ | 729.77 | |
| 37 | 12 | $C_{30}H_{25}N_3O_8S$ | 587.61 | |
| 38 | 13 | $C_{27}H_{29}N_3O_9S$ | 571.61 | |
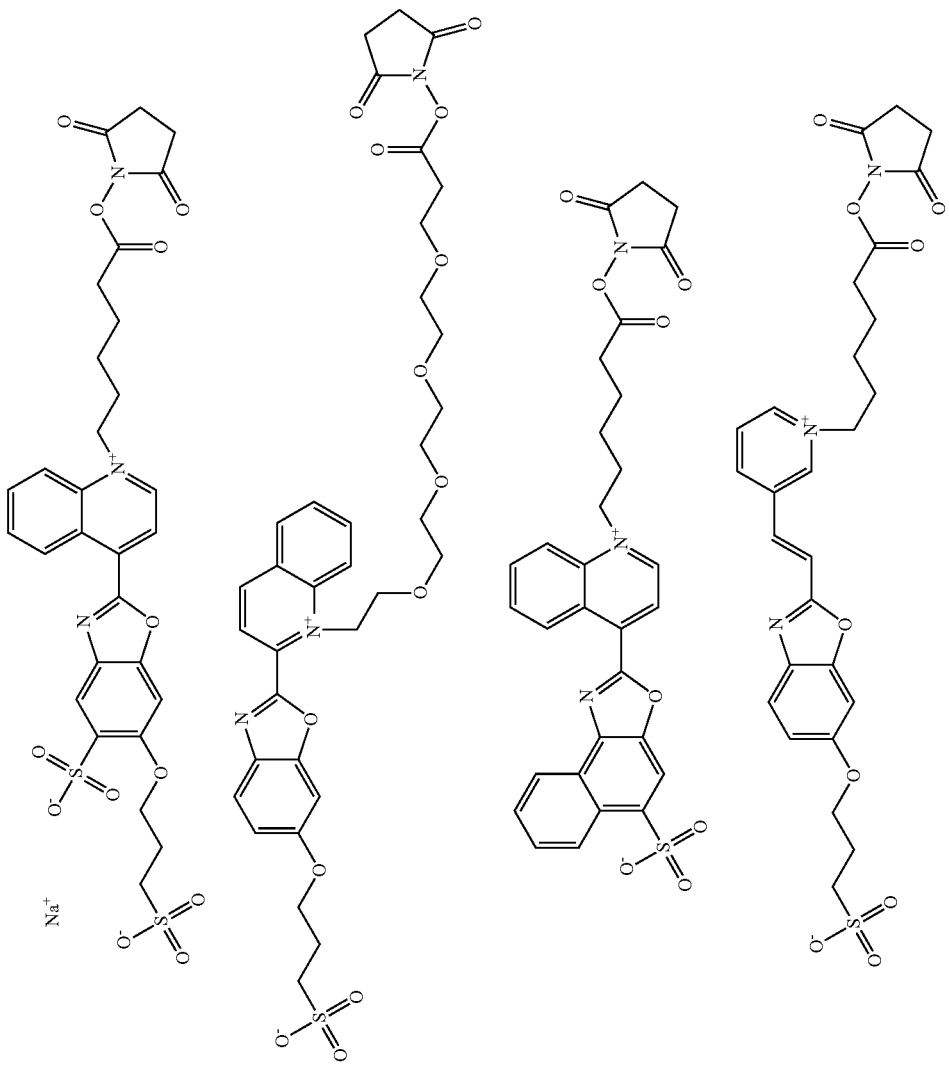

-continued
| Working Example | Starting compound | Empirical formula | Molar mass [g/mol] | NHS ester |
|---|---|---|---|---|
| 39 | 14 | $C_{23}H_{24}N_3O_6Br$ | 518.36 | |
| 40 | 15 | $C_{23}H_{23}N_3O_9S$ | 517.52 | |
| 41 | 17 | $C_{24}H_{24}N_4O_9S$ | 544.54 | |
| 42 | 18 | $C_{25}H_{27}N_4O_7Br$ | 575.42 | |
| 43 | 19 | $C_{26}H_{29}N_5O_9S$ | 587.61 | |
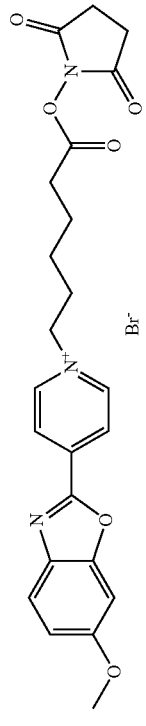

-continued

| Working Example | Starting compound | Empirical formula | Molar mass [g/mol] | NHS ester |
|---|---|---|---|---|
| 44 | 20 | C$_{28}$H$_{33}$N$_4$O$_{11}$S$_2$Na | 688.71 | |
| 45 | 21 | C$_{29}$H$_{34}$N$_5$O$_{12}$S$_2$Na | 731.74 | |
| 46 | 22 | C$_{26}$H$_{22}$N$_3$O$_{11}$S$_2$Na | 639.60 | |

-continued

| Working Example | Starting compound | Empirical formula | Molar mass [g/mol] | | |
|---|---|---|---|---|---|
| 47 | 23 | $C_{31}H_{26}N_3O_{10}S_2Na$ | 687.68 | | NHS ester |
| 48 | 24 | $C_{30}H_{24}N_3O_{11}S_2Na$ | 689.66 | | |

-continued
| Working Example | Starting compound | Empirical formula | Molar mass [g/mol] | |
|---|---|---|---|---|
| 49 | 25 | $C_{26}H_{22}N_3O_{11}S_2Na$ | 639.60 | 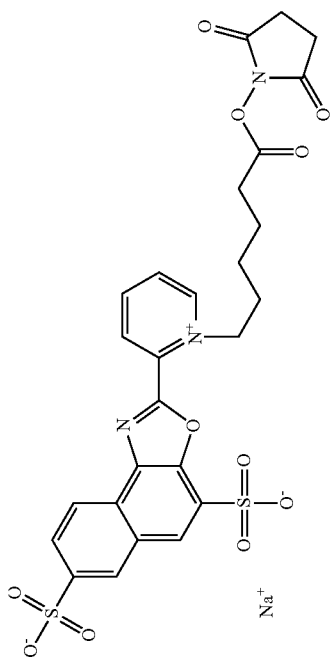 NHS ester |

Working Example 50

Maleimide of Compound 1

70 mg of compound 26 are dissolved in 3 ml of DMF. This is followed by the admixture at room temperature of 44 µl of DIPEA and 36 mg of N-(2-aminoethyl)maleimide trifluoroacetate and stirring for 1 hour. The solvent is distilled off in vacuo and the residue is purified via an RP column.

Yield: 53 mg (72%) ($C_{27}H_{30}N_4O_8S$, 570.63 g/mol)

MS ESI+(m/z): 571 (30%, [M+H]$^+$), 593 (base, [M+Na])

UV-Vis in PBS: $\lambda_{max}$: 383 nm, $\lambda_{em}$: 516 nm, c=21.500 l/mol*cm

Working Example 51

Amine of Compound 25

145 mg of ethylenediamine dihydrochloride are dissolved in 500 µl of water, and the solution is admixed with 95 µl of DIPEA and added at 0° C. to a solution of 70 mg of compound 49 in 3 ml of DMF. This reaction solution is stirred for 20 minutes at 0° C. and for 20 minutes at room temperature. The solvent is distilled off in vacuo and the residue is purified via an RP column.

Yield: 39 mg (63%) ($C_{24}H_{26}N_4O_8S$, 562.62 g/mol)

MS ESI−(m/z): 561 (base, [M−H]$^-$)

UV-Vis in PBS: $\lambda_{max}$: 369 nm, $\lambda_{em}$: 476 nm, c=13.800 l/mol*cm, QY: 0.85

Working Example 52

Figure 1B:
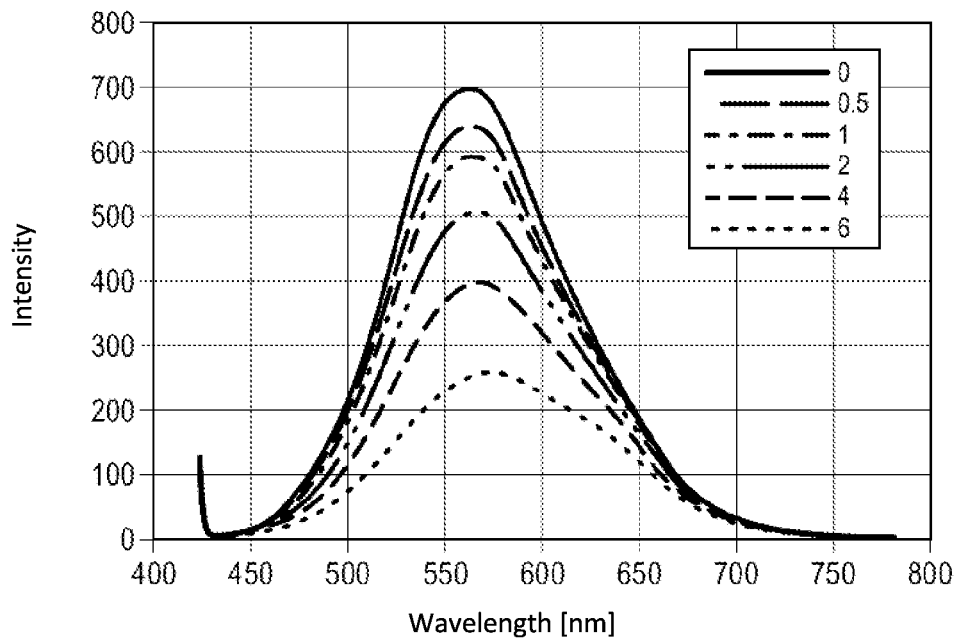
Figure 2:
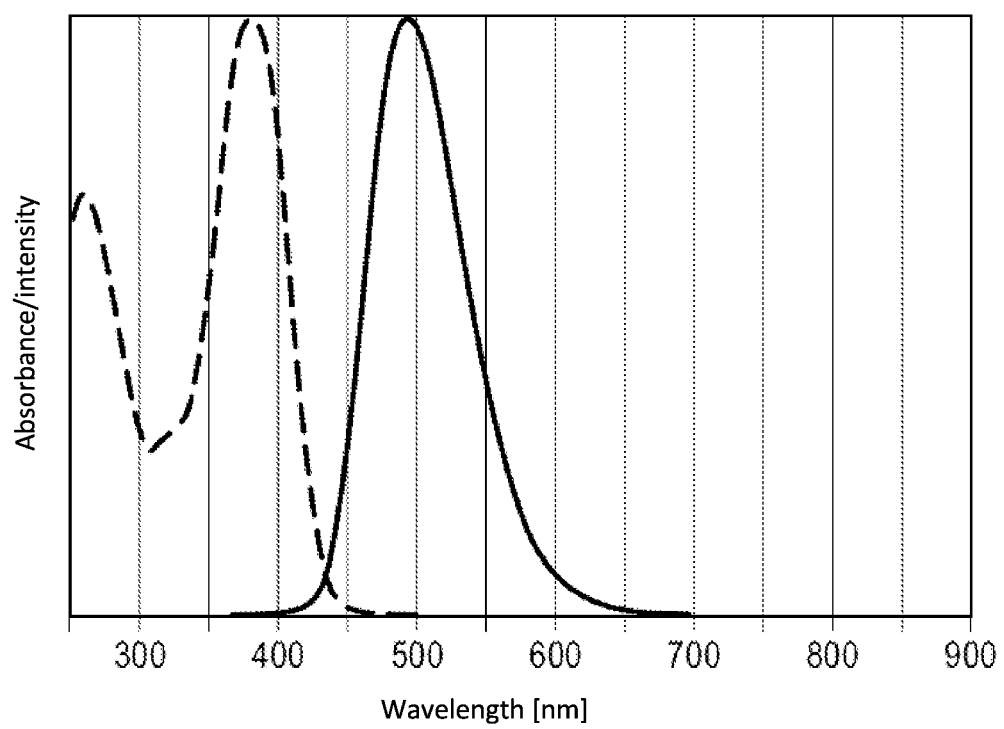
Figure 3:
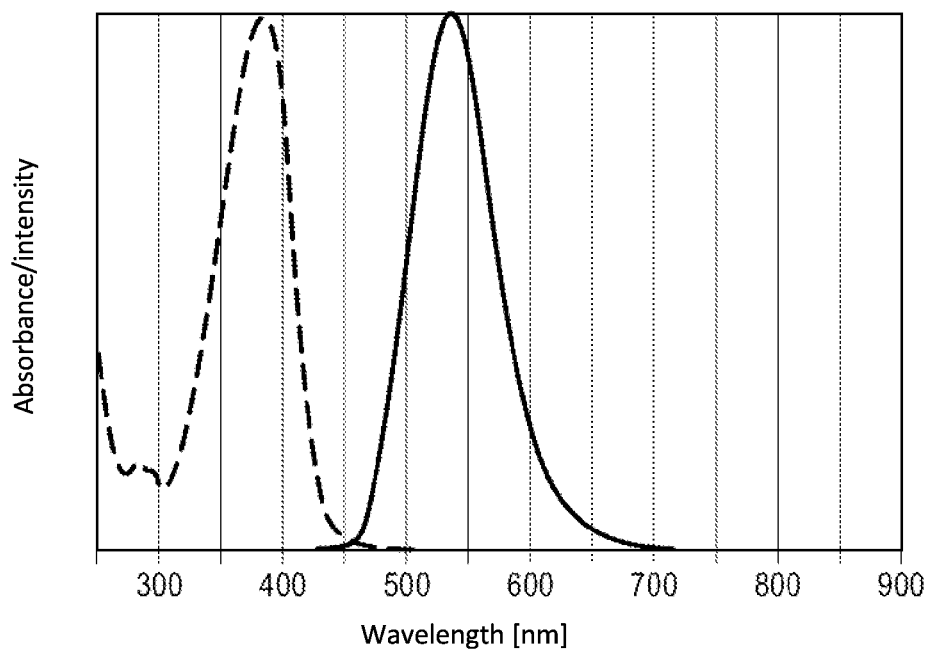
Figure 4:
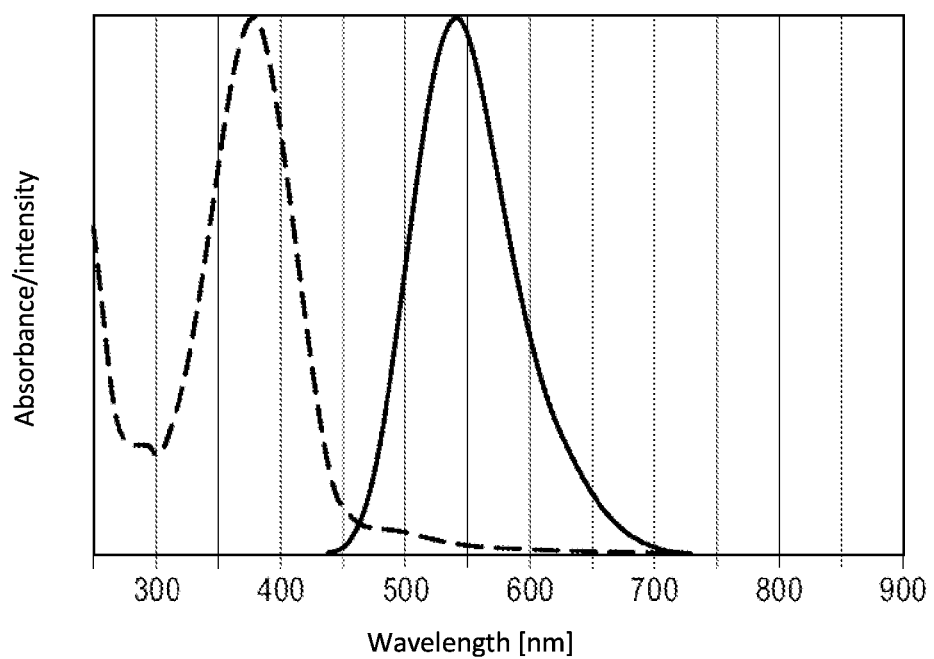
Figure 5:
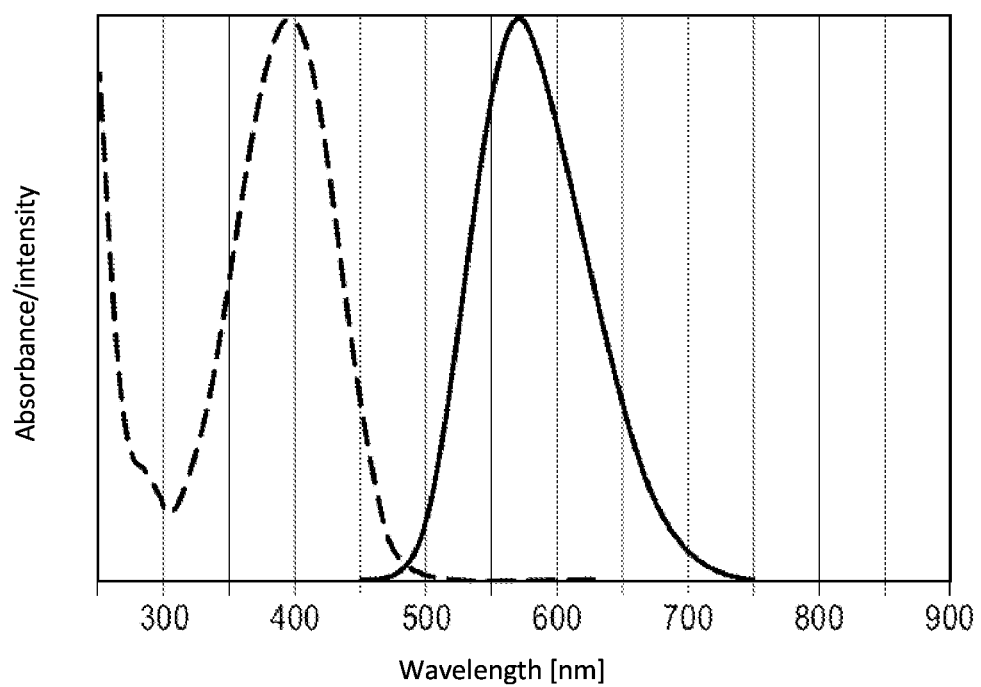
Figure 6:
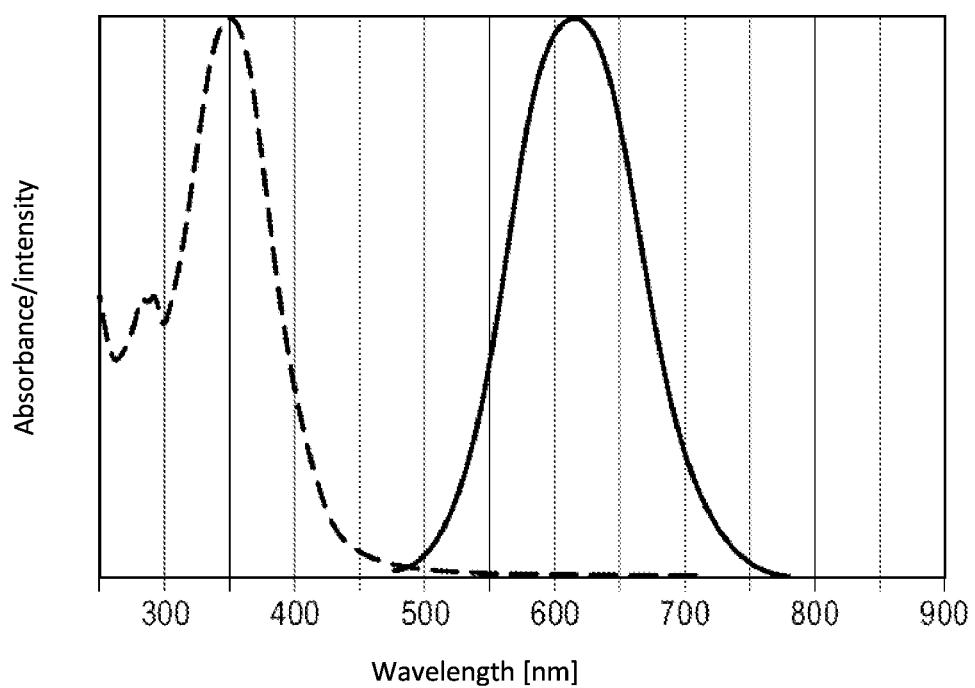

Titrating a streptavidin conjugate of compound 19 with the biotin-DYQ-1-quencher conjugate (cf. FIGS. 1A and 1B)

A 4.7 µM solution of a streptavidin conjugate of compound 19 in PBS was gradually admixed with a DYQ-1-biotin solution (2.5 mM in PBS) using amount-of-substance ratios of 1:0, 1:0.5, 1:1, 1:2, 1:4 and 1:6, all based on streptavidin vs. DYQ-1-quencher. The spectral result of the titration is shown in FIG. 1A. To exclude a wrong positive result due to the fluorescent signal of the streptavidin conjugate being reabsorbed by the increasing amount of DYQ-1-biotin, a blank of an equal amount of streptavidin conjugate of compound 19 was titrated with the same amounts-of-substance as above of the unconjugated DYQ-1-quencher. The spectral result is depicted in FIG. 1B.

It is plainly apparent that the quenching of the emission of the streptavidin conjugate of compound 19 by the DYQ-1-biotin is distinctly more efficient than in the case of the unconjugated quencher, suggesting a successful transfer of energy between compound 19, as donor, and DYQ-1-biotin, as acceptor.

Figure 7:
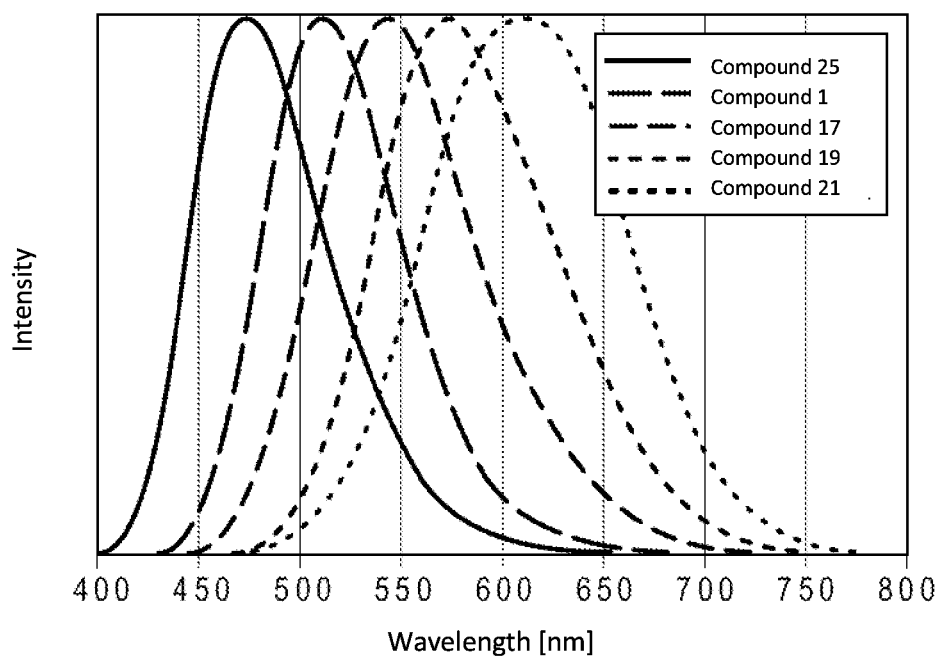

Emission spectra of compounds 1, 17, 19, 21 and 25 according to the present invention are shown in FIG. 7 and identified by different kinds of line as per the legend.

What is claimed is:

1. A compound of general structure or a salt thereof, wherein n=0 or 1 and Z is either
4 pyridyl to form structure I, or
3-pyridyl to form structure II, or
2-pyridyl to form structure III,
and R2 and/or R7 are each a group A bound via a linker L, wherein A is an amine (—NH$_2$), hydroxy (—OH) or phosphoramidite function (—O—P—[O—CH$_2$—CH$_2$—CN]—N[(CH(CH$_3$)$_2$]$_2$), a carboxylic acid (—COOH), an active ester of a carboxylic acid selected from N-hydroxysuccinimidyl (NHS) ester, sulfo-NHS ester, tetrafluorophenyl ester, and p-sulfotetrafluorophenyl ester; a carboxylic acid hydrazide (—CONHNH$_2$); or a carboxylic acid amide (—CONHR12) where R12 is —(CH$_2$)$_t$—Y, wherein Y is —OH, —NH$_2$, —NH$_3^+$, maleimide (—N[CO—CH]$_2$), —NCS, —NCO, —NH—CO—CH$_2$—I, —NH—CO—CH$_2$—Br, azide (—N3), alkyne (—CCH) or phosphoramidite (—O—P—[O—CH$_2$—CH$_2$—CN]—N—[CH—(CH$_3$)$_2$]$_2$), and t represents a number from 1 to 10, and L is a linker selected from —(CH$_2$)$_s$—, —[(CH$_2$)$_m$—O]$_p$—(CH$_2$)$_m$—, NR10-(CH$_2$)$_s$—, —O—(CH$_2$)$_s$—, —S—(CH$_2$)$_s$—, —NR10-C(O)—(CH$_2$)$_s$—, —NR10-C(O)—O—(CH$_2$)$_s$—, —NR10-C(O)—NR11-(CH$_2$)$_s$— or —SO$_2$—NR10-(CH$_2$)$_s$—, wherein R10 and R11 are each independently hydrogen, alkyl and alkoxy-alkyl (—[(CH$_2$)$_m$—O]$_p$—CH$_3$), ω-sulfoalkyl (—(CH$_2$)$_r$—SO$_3$), m represents a number from 2 to 5, and p, r and s each independently represent numbers from 1 to 10.

2. The compound of claim 1 of structure I or a salt thereof, wherein

R1 and R3-R6 are each independently hydrogen, halogen or a sulfonic acid moiety, R2 is ω-sulfoalkoxy (—O—(CH$_2$)$_r$—SO$_3$), alkoxy, polyalkoxy (—O—[(CH$_2$)$_m$—O]$_p$—CH$_3$), an amine function (—NR8R9), wherein R8 and R9 are each independently hydrogen, alkyl, ω-sulfoalkyl (—(CH$_2$)$_r$—SO$_3$), —CO-alkyl, —CO—NR10-alkyl or —CO—O-alkyl, or is equal to -LA where L is —NR10-C(O)—(CH$_2$)$_s$—, —NR10-C(O)—NR11-(CH$_2$)$_s$—, R10 and R11 are each independently hydrogen, alkyl, alkoxy, polyalkoxy (—O—[(CH$_2$—O)$_m$]$_p$—CH$_3$) or ω-sulfoalkyl (—(CH$_2$)$_r$—SO$_3$), R7 is -LA where L is —(CH$_2$)$_s$— or —[(CH$_2$)$_m$—O]$_p$—(CH$_2$)$_m$— or equal to ω-sulfoalkyl (—(CH$_2$)$_r$—SO$_3$), m is a number from 2 to 5, and p, r and s are each independently a number from 1 to 10.

3. The compound of claim 1 of structure I or a salt thereof, wherein

R1, R2, R5 and R6 are each hydrogen or a sulfonic acid moiety, and

R3-R4 are bridged —(CR13=CR14)$_2$-, wherein R13 and R14 are each independently hydrogen and/or a sulfonic acid moiety, R7 is -LA where L is —(CH$_2$)$_s$— or —[(CH$_2$)$_m$—O]$_p$—(CH$_2$)$_m$—, m is a number from 2 to 5, and p and s are each independently numbers from 1 to 10.

4. The compound of claim 1 of structure I or a salt thereof where, wherein

R1, R3 and R4 are each hydrogen, halogen or a sulfonic acid moiety, and

R5-R6 are bridged —(CR13=CR14)$_2$-, wherein R13 and R14 are each independently hydrogen and/or a sulfonic acid moiety, R2 is sulfoalkoxy (—O—(CH$_2$)$_r$—SO$_3$), alkoxy or polyalkoxy (—O—[(CH$_2$)$_m$—O]$_p$—CH$_3$), R7 is -LA where L is —(CH$_2$)$_s$— or —[(CH$_2$)$_m$—O]$_p$—(CH$_2$)$_m$—, m is a number from 2 to 5, and p, r and s are each independently a number from 1 to 10.

5. The compound of claim 1 of structure I or a salt thereof, wherein

R1 and R2 are each hydrogen or a sulfonic acid moiety, and

R3-R4 and R5-R6 are bridged —(CR13=CR14)$_2$-, wherein R13 and R14 are each independently hydrogen and/or a sulfonic acid moiety, R7 is -LA where L is —(CH$_2$)$_s$— or —[(CH$_2$)$_m$—O]$_p$—(CH$_2$)$_m$—, m is a number from 2 to 5, and p and s are each independently numbers from 1 to 10.

6. The compound of claim 1 of structure II or a salt thereof, wherein

R1 and R3-R6 are each independently hydrogen, halogen or a sulfonic acid moiety, R2 is ω-sulfoalkoxy (—O—(CH$_2$)$_r$—SO$_3$), alkoxy, polyalkoxy (—O—[(CH$_2$)$_m$—O]$_p$—CH$_3$), an amine function (—NR8R9), wherein R8 and R9 are each independently hydrogen, alkyl, ω-sulfoalkyl (—(CH$_2$)$_r$—SO$_3$), —CO-alkyl, —CO—NR10-alkyl or —CO—O-alkyl or is equal to -LA where L is —NR10-C(O)—(CH$_2$)$_s$—, —NR10-C(O)—NR11-(CH$_2$)$_s$—, R10 and R11 are each independently hydrogen, alkyl, alkoxy, polyalkoxy (—O—[(CH$_2$—O)$_m$]$_p$—CH$_3$) or ω-sulfoalkyl (—(CH$_2$)$_r$—SO$_3$), R7 is -LA where L is —(CH$_2$)$_s$— or —[(CH$_2$)$_m$—O]$_p$—(CH$_2$)$_m$— or is equal to ω-sulfoalkyl (—(CH$_2$)$_r$—SO$_3$), m is a number from 2 to 5, and p, r and s are each independently numbers from 1 to 10.

7. The compound of claim 1 of structure III or a salt thereof, wherein

R1 and R3-R6 are each independently hydrogen, halogen or a sulfonic acid moiety, R2 is ω-sulfoalkoxy (—O—(CH$_2$)$_r$—SO$_3$), alkoxy, polyalkoxy (—O—[(CH$_2$)$_m$—O]$_p$—CH$_3$), an amine function (—NR8R9), wherein R8 and R9 are each independently hydrogen, alkyl, ω-sulfoalkyl (—(CH$_2$)$_r$—SO$_3$), —CO-alkyl or —O—CO-alkyl or is equal to -LA where L is —NR10-C(O)—(CH$_2$)$_s$—, —NR10-C(O)—NR11-(CH$_2$)$_s$—, R10 and R11 are each independently hydrogen, alkyl, alkoxy, polyalkoxy (—O—[(CH$_2$—O)$_m$]$_p$—CH$_3$) or ω-sulfoalkyl (—(CH$_2$)$_r$—SO$_3$), R7 is -LA where L is —(CH$_2$)$_s$— or —[(CH$_2$)$_m$—O]$_p$—(CH$_2$)$_m$— or is equal to ω-sulfoalkyl (—(CH$_2$)$_r$—SO$_3$), m is a number from 2 to 5, and p, r and s are each independently numbers from 1 to 10.

8. The compound of claim 1 of structure III or a salt thereof, wherein

R1, R2, R5 and R6 are each hydrogen or a sulfonic acid moiety, and

R3-R4 are bridged —(CR13=CR14)$_2$-, wherein R13 and R14 are each independently hydrogen and/or a sulfonic acid moiety, R7 is -LA where L is —(CH$_2$)$_s$— or —[(CH$_2$)$_m$—O]$_p$—(CH$_2$)$_m$—, m is a number from 2 to 5, and p and s are each independently numbers from 1 to 10.

9. The compound of claim 1 of structure III or a salt thereof, wherein

R1, R3 and R4 are each hydrogen, halogen or a sulfonic acid moiety, and

R5-R6 are bridged —(CR13=CR14)$_2$-, wherein R13 and R14 are each independently hydrogen and/or a sulfonic acid moiety, R2 is ω-sulfoalkoxy (—O—(CH$_2$)$_r$—SO$_3$), alkoxy or polyalkoxy (—O—[(CH$_2$)$_m$—O]$_p$—CH$_3$), R7 is -LA where L is —(CH$_2$)$_s$— or —[(CH$_2$)$_m$—O]$_p$—(CH$_2$)$_m$—, m is a number from 2 to 5, an p, r and s are each independently numbers from 1 to 10.

10. The compound of claim 1 of structure III or a salt thereof, wherein

R1 and R2 are each hydrogen or a sulfonic acid moiety, and

R3-R4 and R5-R6 are bridged —(CR13=CR14)$_2$-, wherein R13 and R14 are each independently hydrogen and/or a sulfonic acid moiety, R7 is -LA where L is —(CH$_2$)$_s$— or —[(CH$_2$)$_m$—O]$_p$—(CH$_2$)$_m$—, m is a number from 2 to 5, and p and s are each independently numbers from 1 to 10.

11. The compound of claim 1, where A represents an active ester of a carboxylic acid selected from NHS ester, sulfo-NHS ester, tetrafluorophenyl ester, and p-sulfotetrafluorophenyl ester.

12. The compound of claim 1, where A represents a carboxylic acid (—COOH); a carboxylic acid hydrazide (—CONHNH$_2$); or a carboxylic acid amide (—CONHR12) where R12 is —(CH$_2$)$_r$—Y, wherein Y is —OH, —NH$_2$, —NH$_3^+$, maleimide (—N[CO—CH]$_2$), —NCS, —NCO, —NH—CO—CH$_2$—I, —NH—CO—CH$_2$—Br, azide (—N3), alkyne (—CCH) or phosphoramidite (—O—P—[O—CH$_2$—CH$_2$—CN]—N—[CH—(CH$_3$)$_2$]$_2$), and t represents a number from 1 to 10.

13. The compound of claim 1, wherein A is a group of the formula

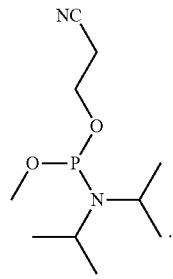

* * * * *